United States Patent
Hanna et al.

(10) Patent No.: US 10,526,358 B2
(45) Date of Patent: Jan. 7, 2020

(54) CRYSTALLINE FORMS

(71) Applicant: GRUNENTHAL GMBH, Aachen (DE)

(72) Inventors: Mazen Hanna, Lutz, FL (US); Ning Shan, Chandler, AZ (US); David R. Weyna, Tampa, FL (US); Miranda L. Cheney, Northborough, MA (US)

(73) Assignee: THAR PHARMA, LLC, Pittsburgh, PA (US)

( * ) Notice: Subject to any disclaimer, the term of this patent is extended or adjusted under 35 U.S.C. 154(b) by 0 days.

(21) Appl. No.: 16/186,772

(22) Filed: Nov. 12, 2018

(65) Prior Publication Data

US 2019/0144474 A1 May 16, 2019

Related U.S. Application Data

(63) Continuation of application No. PCT/IB2017/000621, filed on May 10, 2017.

(60) Provisional application No. 62/336,075, filed on May 13, 2016.

(51) Int. Cl.

| C07F 9/6506 | (2006.01) |
| C07C 229/22 | (2006.01) |
| C07C 229/24 | (2006.01) |
| A61K 9/00 | (2006.01) |
| A61P 35/04 | (2006.01) |
| A61P 19/10 | (2006.01) |
| A61P 3/14 | (2006.01) |

(52) U.S. Cl.
CPC .............. *C07F 9/6506* (2013.01); *A61P 3/14* (2018.01); *A61P 19/10* (2018.01); *A61P 35/04* (2018.01); *C07C 229/22* (2013.01); *C07C 229/24* (2013.01); *A61K 9/0053* (2013.01); *C07B 2200/13* (2013.01)

(58) Field of Classification Search
CPC ... C07F 9/6506; C07C 229/22; C07C 229/24; A61P 3/14; C07B 200/13
See application file for complete search history.

(56) References Cited

U.S. PATENT DOCUMENTS

2007/0134319 A1* 6/2007 Zannou ................ A61K 9/1075
424/464

FOREIGN PATENT DOCUMENTS

| WO | 00/61111 A1 | 10/2000 | |
| WO | WO-0061111 A1 * | 10/2000 | ........... A61K 31/663 |

OTHER PUBLICATIONS

Rouhi, Chemical and Engineering News, The Right Stuff, 2003, 81(8), pp. 32-35. (Year: 2003).*
Hursthouse et al, Organic Process Research & Development, Why Do Organic Compounds Crystallize Well or Badly or Ever so Slowly? Why is Crystallization Nevertheless Such a Good Purification Technique?, 2009, 13, 1231-1240. (Year: 2009).*
International Search Report and Written Opinion in International Application No. PCT/IB2017/000621, dated Nov. 16, 2017.
International Preliminary Report on Patentability in International Application No. PCT/IB2017/000621, dated Nov. 22, 2018.

* cited by examiner

*Primary Examiner* — Paul A Zucker
(74) *Attorney, Agent, or Firm* — J.A. Lindeman & Co. PLLC; Jeffrey Lindeman; Aaron Raphael

(57) ABSTRACT

The invention relates to the preparation and characterization of novel forms of (1-hydroxy-2-imidazol-1-yl-1-phosphono-ethyl) phosphonic acid. The invention also relates to the use of the novel forms of (1-hydroxy-2-imidazol-1-yl-1-phosphono-ethyl) phosphonic acid in pharmaceutical compositions in drug delivery systems for humans. The invention further relates to the use of the novel forms of (1-hydroxy-2-imidazol-1-yl-1-phosphono-ethyl) phosphonic acid or the pharmaceutical compositions thereof to treat and/or prevent a disease state associated with osteoporosis, tumor induced hypercalcemia (TIH), cancer-induced bone metastasis, Paget's disease or for adjuvant or neoadjuvant therapies.

18 Claims, 23 Drawing Sheets

CRYSTALLINE FORMS

FIELD OF THE INVENTION

This disclosure pertains to generating novel crystalline forms of (1-hydroxy-2-imidazol-1-yl-1-phosphono-ethyl) phosphonic acid, in which such forms include but are not limited to cocrystals, salts, hydrates, solvates, solvates of salts, and mixtures thereof. Methods for the preparation and pharmaceutical compositions suitable for drug delivery systems that include one or more of these new forms are disclosed.

BACKGROUND OF THE INVENTION

Zoledronic acid, known as (1-hydroxy-2-imidazol-1-yl-1-phosphono-ethyl)phosphonic acid, is depicted by the following chemical structure:

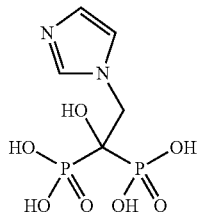

Zoledronic acid is a third generation bisphosphonate which far exceeds the previous generations in terms of efficacy and is used predominately for indications of osteoporosis, Paget's disease, hypercalcemia, and inhibition of bone metastasis. It was originally developed by Novartis and marketed as the monohydrate under the brand names Zometa® and Reclast®. Zoledronic acid was first approved in 2000 for the treatment of hypercalcemia in Canada. It was later approved for use in the US for hypercalcemia in 2001, for multiple myeloma and bone metastases from solid tumors in 2002, and for osteoporosis and Paget's disease in 2007. Clinical trials have also been conducted or are ongoing exploring the use of zoledronic acid in neoadjuvant or adjuvant cancer therapy, Coleman, et al., British J Cancer 2010; 102(7):1099-1105, Gnant, et al., New England J Medicine. 2009, 360 (17):679-691 and Davies, et al. J Clinical Oncology, 2010, 28(7s): Abstract 8021. Zoledronic acid is administered as an intravenous (IV) dose of 4 mg over 15 minutes per month for hypercalcemia of malignancy, multiple myeloma, and bone metastases from solid tumors, while an IV dose of 5 mg over 15 minutes is used for osteoporosis and Paget's disease.

Zoledronic acid is sparingly soluble in water and 0.1 N HCl solution but is freely soluble in 0.1 N NaOH. Zoledronic acid is practically insoluble in various organic solvents.

Much effort has been taken to generate novel oral formulations of zoledronic acid through crystallization and metal salt formation to improve its aqueous solubility, permeability, and subsequent oral bioavailability. A crystalline trihydrate was disclosed in the U.S. Patent application 2006/0178439 A1 and world patent application WO2007/032808. Seven hydrated forms, an amorphous form, three monosodium salts, and eleven disodium salts with varying degrees of hydration of zoledronic acid were also disclosed in the patent application WO2005/005447 A2. Zoledronate metal salts including $Na^+$, $Mg^{2+}$, $Zn^{2+}$ were reported in the journal of Drugs of the Future (Sorbera et al, 25(3), *Drugs of the Future*, (2000)). Zoledronate, zoledronic, or zoledronic salt represents the ionic form of zoledronic acid. Patent application WO2008/064849 A1 from Novartis disclosed additional metal salts including two Ca' salts, two $Zn^{2+}$ salts, one $Mg^{2+}$ salt, as well as a monohydrate, a trihydrate, an amorphous form, and an anhydrous form.

According to the US Food and Drug Administration (FDA) Summary Basis of Approval (SBA) for zoledronic acid, the poor oral bioavailability (approximately 1%), is partially due to its poor permeability in the GI tract. It was also noted that insoluble metal complexes were formed in the upper intestines, most commonly with calcium. Zoledronic acid has also been shown to cause severe gastric and intestinal irritations. In some cases the irritations were so severe that medical treatment was required.

Due to the fact that zoledronic acid is only available as a parenteral dosage form there is a clear need to develop novel forms of zoledronic acid that can be included in an oral dosage form particularly as the use of orally administered drugs are becoming more wide spread in many therapeutic areas including the treatment of cancer. The upward trend in the use of oral drugs will continue especially in light of the goal to decrease the overall cost of healthcare. Thus, there is an opportunity to create oral dosage forms of IV drugs where oral dosage forms do not yet exist due to their poor aqueous solubility and/or poor permeability providing a clear clinical benefit for patients.

Recent activity concerning the development of oral formulations has led to the use of medium chain fatty acids to enhance the drug's low permeability as disclosed in the US 2007/0134319 A1 and US 2007/0196464 patent applications. Additionally, Acylcarnitines have also been used for the same purpose as published in WO 00/61111 and P. Sinko et al; Pharmaceutical Research, Vol. 16, No. 4, 1999, P 527-533. Modified amino acid carriers, have also been employed to improve the absorption of the drug as shown in the WO 2007/093226 A1 application.

The development of oral forms of zoledronic acid has been problematic due to its poor aqueous solubility and permeability. By using pharmaceutically acceptable cocrystal formers to bond with pure zoledronic acid to create novel molecular complexes neutral and ionic (e.g. cocrystals, salts and solvates) which can improve solubility and/or permeability, the opportunity is therefore provided to tackle such problems and develop an oral dosage form.

All of the above attempts to improve the oral bioavailability of zoledronic acid were either focused on improving the aqueous solubility by generating novel solid forms, or by mixing the drug with an inactive ingredient that has enhanced GI tract permeability. The improvement of aqueous solubility failed to improve the bioavailability of zoledronic acid, since the formation of insoluble zoledronate calcium complexes is unlikely to be prevented. On the other hand, powder mixtures of the poorly permeable drug with inactive permeability enhancers improved the bioavailability of the drug. This approach of mixing different materials with different particle sizes and size distributions could result in poor blend/physical mixture uniformity. Constituents of the mixture could also segregate during transportation or with shaking and vibration. Additionally, the powder blends require that the ingredients are compatible and no potential for solid-solid interaction with or without atmospheric interferences exist thus impacting on their physical stability during storage or in a delivery system.

To the best of the inventors' knowledge, no attempt has been made prior to this invention towards a deliberate molecular design to create a molecular complex of the drug and additional component(s) (coformer(s)) in a single crystalline structure that is physically stable and is not influenced by the addition of excess coformer(s) in the formulation. The benefit of such design can lead to the elimination of all potential physical instability in the physical mix of the molecular complex and the coformer(s). Additionally, the resulting molecular complexes possess very different physicochemical properties compared to the parent drug, coformer or their physical mixture. These properties include but are not limited to melting point, thermal and electrical conductivity, aqueous solubility, rate of dissolution and permeability across the GI tract membrane.

Orally administered drugs are becoming more preferred in various therapeutic areas including cancers. Clearly, there is an opportunity to create oral dosage forms of IV drugs where oral dosage forms do not yet exist due to their poor aqueous solubility and/or poor permeability providing a clear clinical benefit for patients. Given the fact that zoledronic acid is only approved for IV administration, there is a need to develop an oral dosage form of zoledronic acid. By using pharmaceutically acceptable and/or approved coformers to hydrogen bond with zoledronic acid, novel molecular complexes (e.g. cocrystals, salts, solvates, and mixtures thereof) with improve solubility and/or permeability can be created. These novel molecular complexes could be used in the development of an oral dosage form for zoledronic acid.

SUMMARY OF THE INVENTION

The present disclosure is directed towards generating new forms of zoledronic acid, which have the therapeutic efficacy of zoledronic acid discussed above, with improved aqueous solubility, rate of dissolution, and/or improved permeability and thus enhanced bioavailability. One aspect of the present disclosure includes novel molecular complexes of zoledronic acid that includes cocrystals, salts, and solvates (e.g. hydrates and mixed solvates as well as solvates of salts), and mixtures containing such materials. In addition, the disclosure further includes methods for the preparation of such complexes.

The disclosure further includes compositions of molecular complexes of zoledronic acid suitable for incorporation in a pharmaceutical dosage form. Specific molecular complexes pertaining to the disclosure include, but are not limited to, complexes of zoledronic acid and L-carnitine and fatty acid derivatives of L-carnitine including but not limited to; o-palmitoyl-L-carnitine, o-myristoyl-L-carnitine, o-lauroyl-L-carnitine, o-decanoyl-L-carnitine, o-ocatanoyl-L-carnitine. Obvious variants of the disclosed zoledronic acid forms in the disclosure, including those described by the drawings and examples, will be readily apparent to the person of ordinary skill in the art having the present disclosure and such variants are considered to be a part of the current invention.

The foregoing and other features and advantages of the disclosed technology will become more apparent from the following detailed description, which proceeds with reference to the accompanying drawings. Such description is meant to be illustrative, but not limiting, of the invention.

DETAILED DESCRIPTION OF THE PREFERRED EMBODIMENTS

Figure 1:
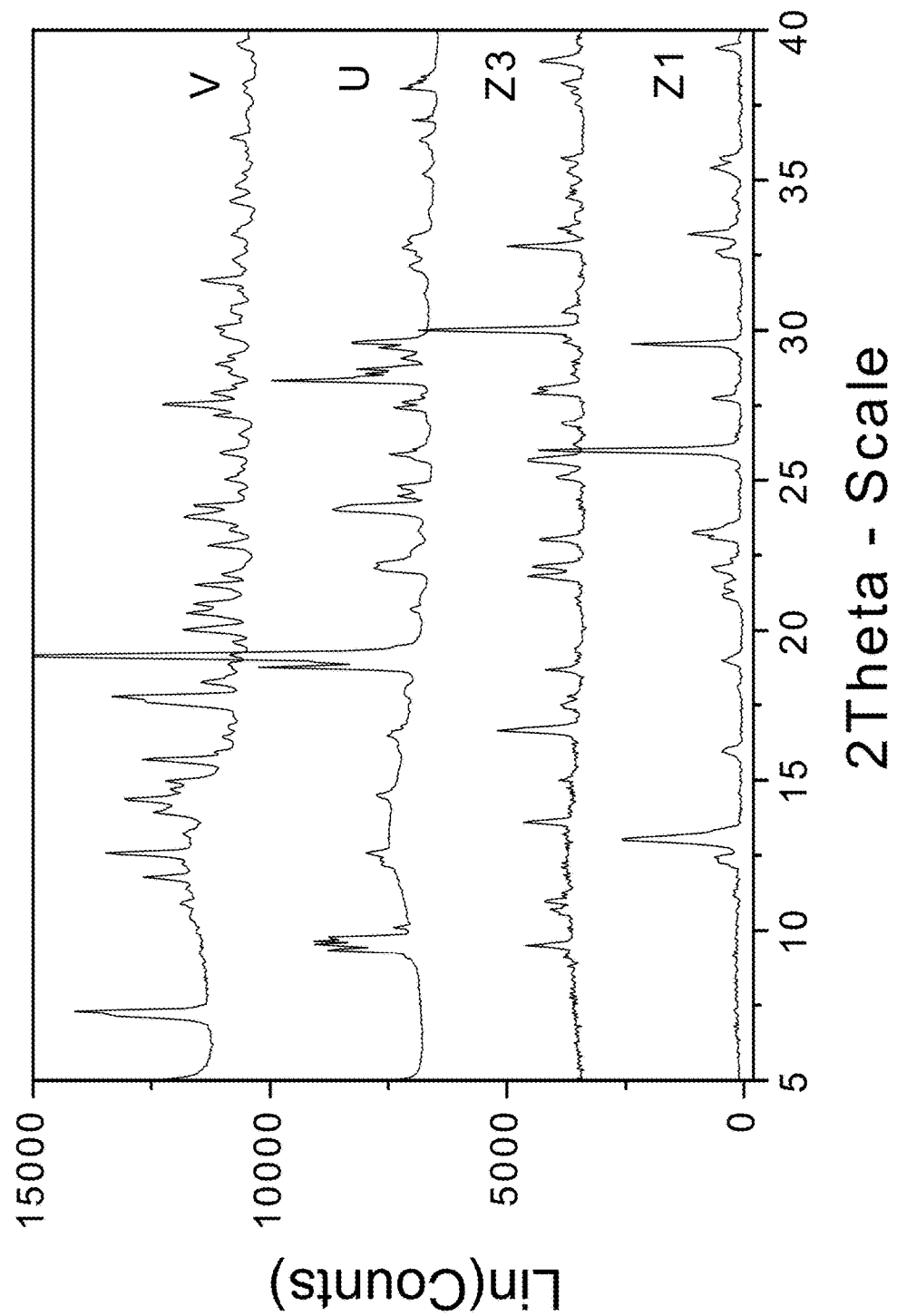
FIG. 1. PXRD diffractograms of: Form V=zoledronic acid, L-carnitine, and water complex from mechanical milling; U=L-carnitine; Z1=Zoledronic acid monohydrate; and Z3=Zoledronic acid trihydrate.

In general, active pharmaceutical ingredients (APIs) in pharmaceutical compositions can exist in a variety of different forms including amorphous forms, solvates, hydrates, cocrystals, salts and polymorphs thereof. The discovery of novel API forms may provide an opportunity to improve the performance characteristics of a pharmaceutical product. Additionally, discovery of novel drug forms expands the array of options available for designing pharmaceutical dosage forms with targeted release profiles or other desirable characteristics.

The alteration of the crystal form of a given API could result in the modification of the physical properties of the target molecule. For example, various polymorphs of a given API can exhibit different aqueous solubilities where the thermodynamically stable polymorph would exhibit a lower solubility than the meta-stable polymorph. Pharmaceutical polymorphs can also differ in properties such as rate of dissolution, shelf life, bioavailability, morphology, vapor pressure, density, color, and compressibility. Accordingly, it is desirable to enhance the properties of an API by forming molecular complexes such as a cocrystal, salt, solvate or hydrate with respect to aqueous solubility, rate of dissolution, bioavailability, $C_{max}$, $T_{max}$, physicochemical stability, down-stream processibility (e.g. flowability compressibility, degree of brittleness, particle size manipulation), decrease in polymorphic form diversity, toxicity, taste, production costs, and manufacturing methods.

During the development of an orally administered drug, it is often advantageous to generate novel crystal forms of such drugs that could possess desirable properties, including increased aqueous solubility and/or stability. In many cases, an increase in the dissolution rate is desirable as it would potentially increase the bioavailability of an API. This also applies to the development of novel forms of zoledronic acid which, when administered orally to a subject, could achieve a similar bioavailability compared to other routes of drug delivery on a dose-for-dose basis.

The present invention provides new crystal forms of zoledronic acid in the form of a zoledronic acid L-carnitine complex, or fatty acid L-carnitine derivatives characterized by PXRD, FTIR, NMR and TGA.

The present invention provides novel zoledronic acid L-carnitine hydrated complex having strong peaks at about 7.3, 12.6, 15.7, 17.8, 27.5±0.2 degrees two-theta.

The present invention also provides a novel crystalline form of a zoledronic acid L-carnitine complex characterized by a PXRD pattern having peaks at about 8.8, 9.6, 13.2, 19.0, 30.4±0.2 degrees two-theta. Both novel forms have apparent water solubilities at room temperature of about 25 mg/ml compared to few mg/ml for pure zoledronic acid.

The present invention provides a new crystal form of zoledronic acid in the form of zoledronic acid, o-palmitoyl-L-carnitine and water complex (1:1:1), characterized by an X-ray powder diffraction pattern having strong peaks at about 6.8, 9.0, 13.5, 20.2, and 22.4±0.2 degrees two-theta.

The present invention provides a new crystal form of zoledronic acid in the form of zoledronic acid, o-myristoyl-L-carnitine and water complex (1:1:1), characterized by an X-ray powder diffraction pattern having strong peaks at about 9.6, 11.9, 14.3, 19.0, and 21.4±0.2 degrees two-theta.

The present invention provides a new crystal form of zoledronic acid in the form of zoledronic acid, o-lauroyl-L-carnitine, and water complex (1:1:1), characterized by an X-ray powder diffraction pattern having strong peaks at about 7.6, 14.1, 14.9, 20.8, and 23.1±0.2 degrees two-theta.

The present invention provides a new crystal form of zoledronic acid in the form of zoledronic acid, o-decanoyl-L-carnitine, and water complex (1:1:1), characterized by an X-ray powder diffraction pattern having strong peaks at about 5.5, 8.1, 13.3, 18.5, and 20.9±0.2 degrees two-theta.

The present invention provides a new crystal form of zoledronic acid in the form of zoledronic acid, o-octanoyl-L-carnitine, and water complex (1:1:1), characterized by an X-ray powder diffraction pattern having strong peaks at about 3.25, 5.8, 11.3, 14.1, and 19.8±0.2 degrees two-theta.

The present invention provides a new crystal form of zoledronic acid in the form of zoledronic acid, o-octanoyl-L-carnitine, and water complex (1:1:1.5), characterized by an X-ray powder diffraction pattern having strong peaks at about 3.3, 6.1, 14.0, 15.0, and 20.9±0.2 degrees two-theta.

The present invention provides a new crystal form of zoledronic acid in the form of zoledronic, L-carnitine, and water complex (1:1:1), characterized by an X-ray powder diffraction pattern having strong peaks at about 9.6, 10.0, 13.2, 18.9, 19.9±0.2 degrees two-theta.

Accordingly, in a first aspect, the present invention includes complexes of zoledronic acid and L-carnitine, and its fatty acid derivatives; o-palmitoyl-L-carnitine, o-myristoyl-L-carnitine, o-lauroyl-L-carnitine, o-decanoyl-L-carnitine, o-octanoyl-L-carnitine which are capable of complexing in the solid-state, for example, through dry or solvent-drop grinding (liquid assisted grinding), heating or solvent evaporation of their solution in single or mixed solvent systems, slurry suspension, supercritical fluids or other techniques known to a person skilled in the art.

Another aspect of the invention provides novel complexes of zoledronic acid and L-carnitine that have been observed by their PXRD patterns which are different from all the previous molecular complexes prepared.

Another aspect of the invention provides zoledronic and o-palmitoyl-L-carnitine complex by dissolving both compounds in water and allowing the solvent mixtures to evaporate to form crystalline material.

Another aspect of the invention provides zoledronic and o-myristoyl-L-carnitine complex by dissolving both compounds in water and allowing the solvent mixtures to evaporate to form crystalline material.

Another aspect of the invention provides zoledronic and o-lauroyl-L-carnitine complex by dissolving both compounds in water and allowing the solvent mixtures to evaporate to form crystalline material.

Another aspect of the invention provides zoledronic and o-decanoyl-L-carnitine complex by dissolving both compounds in water and allowing the solvent mixtures to evaporate to form crystalline material.

Another aspect of the invention provides zoledronic and o-octanoyl-L-carnitine complex by dissolving both compounds in water and allowing the solvent mixtures to evaporate to form crystalline material.

Another aspect of the invention provides a process for scale up of the zoledronic acid:L carnitine and its fatty acid derivatives molecular complexes.

Yet another aspect of the invention provides a process for scale up of the molecular complex from milligram to gram level using a saturated slurry technique.

Another aspect of the invention is improved aqueous solubility of the novel molecular complexes compared to that of the parent molecule.

Derivatization of L-carnitine with fatty acids was performed in-house using the method disclosed in WO 2010/089094 through an esterification reaction with acylchlorides of various chain lengths and L-carnitine HCl. Modifications to the procedure were made as follows; L-carnitine HCl was synthesized from L-carnitine before the esterification and used as the starting material for each L-carnitine fatty acid derivative synthesis.

Another aspect of the invention provides complexes of zoledronic acid and L-carnitine and its fatty acid derivatives; o-palmitoyl-L-carnitine, o-myristoyl-L-carnitine, o-lauroyl-L-carnitine, o-decanoyl-L-carnitine, o-octanoyl-L-carnitine suitable for a pharmaceutical formulation than can be delivered orally to the human body. The pharmaceutical formulation contains a therapeutically effective amount of at least one of the novel molecular complexes of zoledronic acid according to the invention and at least one pharmaceutically acceptable carrier, (also known in the art as a pharmaceutically acceptable excipient). The novel molecular complexes of zoledronic acid are therapeutically useful for the treatment and/or prevention of disease states associated with osteoporosis, tumor induced hypercalcemia (TIH), cancer induced bone metastasis, Paget's disease or for adjuvant or neoadjuvant therapies discussed above.

The invention also relates to methods of treatment using novel molecular complexes of zoledronic acid of the invention or a pharmaceutical formulation containing them. A pharmaceutical formulation of the invention may be in any pharmaceutical form which contains a novel molecular complex of zoledronic acid according to the invention. The pharmaceutical formulation may be, for example, a tablet, capsule, liquid suspension, injectable, suppository, topical, or transdermal. The pharmaceutical formulations generally contain about 1% to about 99% by weight of at least one novel molecular complex of zoledronic acid of the invention and 99% to 1% by weight of a suitable pharmaceutical excipient.

The techniques and approaches set forth in the present disclosure can further be used by the person of ordinary skill in the art to prepare variants thereof, said variants are considered to be part of the inventive disclosure.

EXAMPLES

The following examples illustrate the invention without intending to limit the scope of the invention.

Zoledronic acid as a starting material used in all experiments in this disclosure was supplied by Farmkemi Limited (Wuhan Pharma Chemical Co.), China with purity of ca. 98% and was purified further via recrystallization from water. All other pure chemicals (Analytical Grade) were supplied by Sigma-Aldrich and Fisher and used without further purification.

Solid Phase Characterization

Analytical technique used to observe the crystalline forms included PXRD. The particular methodology used in such analytical techniques should be viewed as illustrative, and not limiting in the context of data collection. For example, the particular instrumentation used to collect data may vary; routine operator error or calibration standards may vary; sample preparation method may vary.

Powder X-Ray Diffraction (PXRD): All zoledronic acid molecular complex products were observed by a D-8 Bruker X-ray Powder Diffractometer using Cu Kα ($\lambda$=1.540562 Å), 40 kV, 40 mA. The data were collected over an angular range of 3° to 40° 2θ in continuous scan mode at room temperature using a step size of 0.05° 2θ and a scan speed of 6.17°/min.

Fourier Transform FTIR Spectroscopy (FTIR): FTIR analysis was performed on a Perkin Elmer Spectrum 100 FTIR spectrometer equipped with a solid-state ATR accessory.

Thermogravimetric Analysis (TGA):

All zoledronic acid molecular complex products were analyzed on a Thermal Analysis Q50 Thermogravimetric analyzer over a temperature range of 30~250° C. and a scan rate of 10° C./minute.

Nuclear Magnetic Resonance (NMR): Carnitines and corresponding hydrochloride salts were analyzed on an Agilent VNMRS 500 MHz with direct drive.

Figure 2:
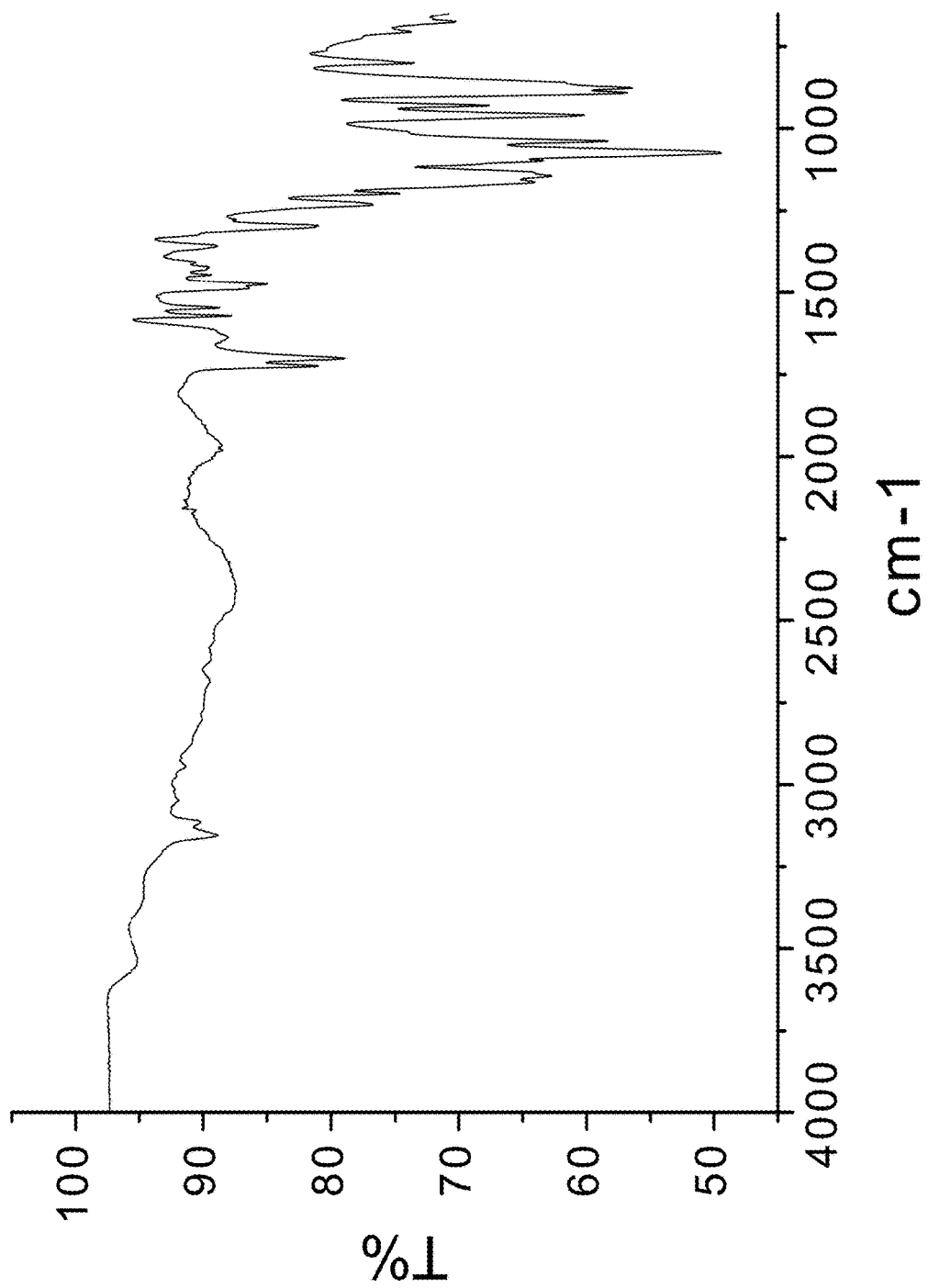
FIG. 2. FTIR spectrum of Form V=zoledronic acid, L-carnitine, and water complex from mechanical milling.

Example 1: Preparation of Zoledronic Acid L-Carnitine and Water Complex by Solvent Drop Grinding A solid mixture of 105 mg of zoledronic acid and 59 mg of L-carnitine was ground via mechanical milling with 50 μL of water. The solids gathered after grinding were stored in a screw cap vial for subsequent analysis. The material was characterized by PXRD and FTIR corresponding to FIG. 1 and FIG. 2, respectively.

Example 2: Preparation of Zoledronic and L-Carnitine Complex by Slurry Technique A powder mixture of 270 mg of zoledronic acid and 150 mg of L-carnitine were slurried overnight in 5 mL of isopropanol. The filtered and dried solids were stored in a screw cap vial for subsequent analysis. The material was characterized by PXRD FIG. 3 and FTIR, FIG. 4

Figure 3:
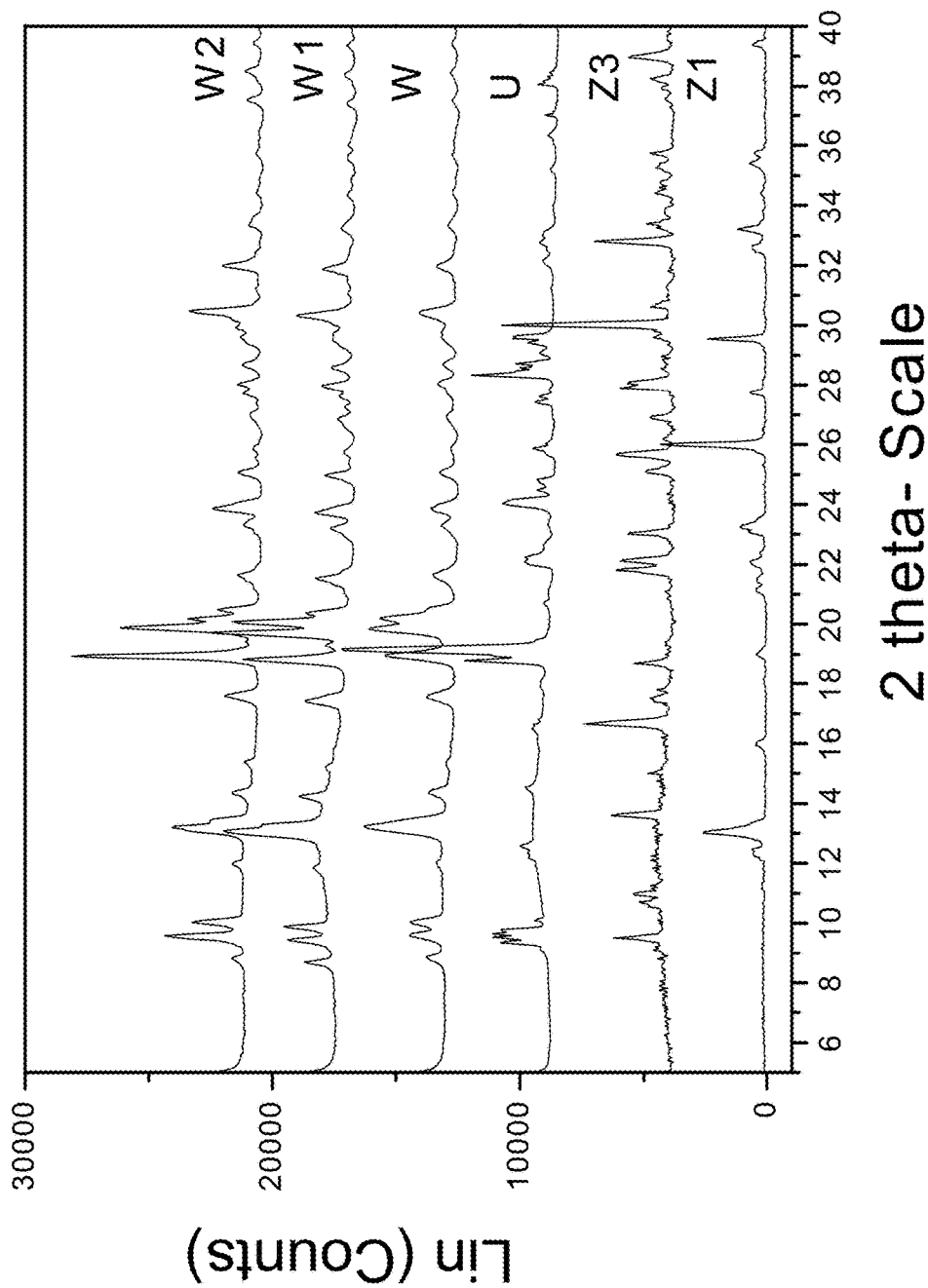
FIG. 3. PXRD diffractograms of: Form W2=zoledronic acid L-carnitine complex from solution evaporation; Form W1=zoledronic acid L-carnitine complex from a large scale saturated slurry; Form W=zoledronic L-carnitine complex from slurry technique; U=L-carnitine; Z1=Zoledronic acid monohydrate; and Z3=Zoledronic acid trihydrate.
Figure 4:
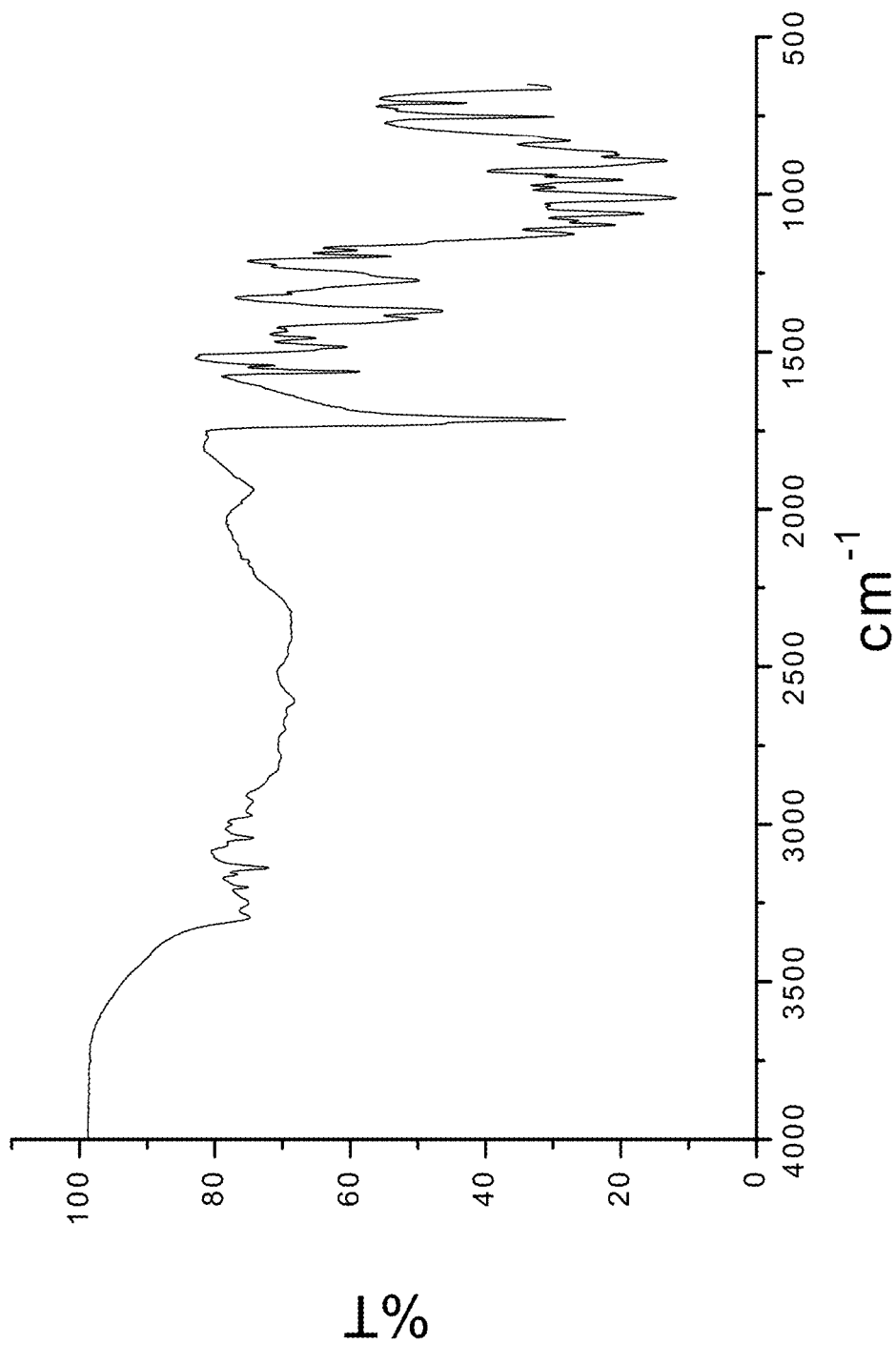
FIG. 4. FTIR spectra of Form W.
Figure 5:
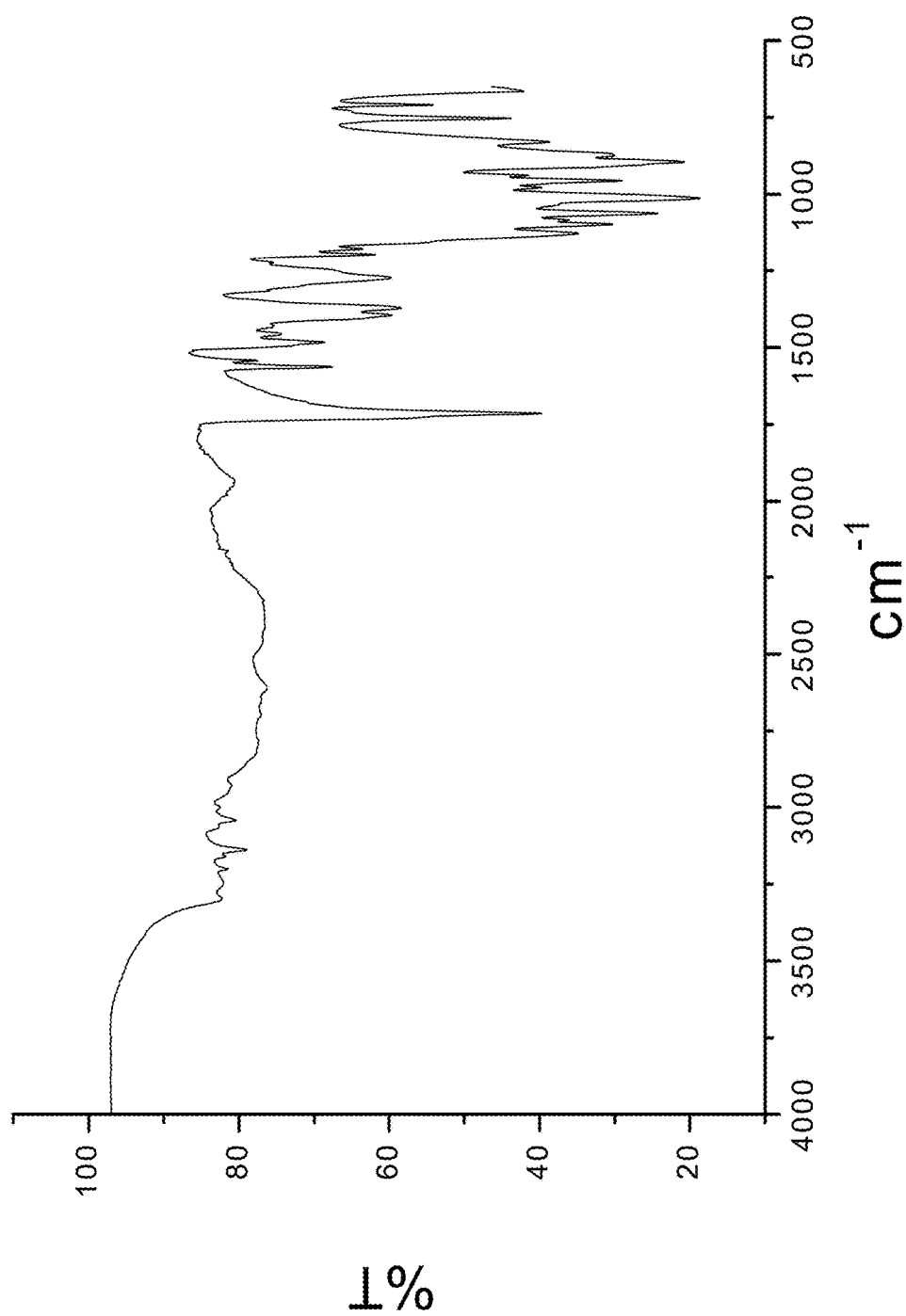
FIG. 5. FTIR spectra of Form W1.

Example 3: Scaled Up Production of Zoledronic and L-Carnitine by Slurry Technique A powder mixture of 3.51 g of zoledronic acid and 1.95 g of L-carnitine were slurried overnight in 50 mL of isopropanol. The filtered and dried solids were stored in a screw cap vial for subsequent analysis. The material was characterized by PXRD and is shown in FIG. 3.

Example 4: Preparation of Zoledronic Acid and L-Carnitine Complex from Solution Evaporation A solid mixture of 270 mg of zoledronic acid and 150 mg of L-carnitine was dissolved in 20 mL of water. It was heated to 50° C. and allowed to evaporate slowly. At dryness the solid was gathered and stored in screw cap vial for subsequent analysis. The material was characterized by PXRD as shown in FIG. 3.

Example 5: Preparation L-Carnitine HCl 100 g of L-carnitine is dried in a vacuum oven at 80-90° C. for 2-3 days or in a phosphorous pentoxide chamber for 5-7 days. Once dry the material is weighed and a slurry is created at 1 g/mL in deionized water. One molar equivalent of concentrated HCl is added and the solid is dissolved. The solution is heated on a hotplate open at 55-60° C. in a shallow container for 5-8 hours until very viscous and then placed in an oven at the same temperature for 12-16 hours until a stiff layer exists or nucleation is visible. The material is then further dried with a vacuum oven at 80-90° C. for 2-3 days until the solid is opaque white and easily flaking off the container. The particulate material was gathered and stored in a desiccator with phosphorus pentoxide for subsequent analysis. The material was characterized by proton NMR, 500 MHz, Methanol, δ 2.57 (dd, 1H); 3.25 (s, 9H); 3.48 (m, 3H); 4.58 (m, 1H).

Example 6: Preparation of o-Palmitoyl-L-Carnitine HCl Monohydrate 5 g of L-carnitine HCl is placed into a 100 mL round bottom flask with a Teflon coated stir bar a glass stopper inside a chemical hood followed by chloroacetic acid (2.62 mol per mol of L-carnitine HCl) into the same flask. Heat at 70° C. until a clear solution exists. Lift from heat and add palmitoyl chloride slowly over 1 hour replacing stopper in between additions. Let cool 5-10 min and add acetone (34 mol acetone of L-carnitine HCl) to precipitate out product as white solid. Let stand for 10 minutes and then filter off solid. Dry under vacuum at 50°-60° C. for 12-24 hrs or for 24-48 hrs in an oven at 55-60° C. and check by TGA. Store in a refrigerator or desiccator for subsequent use. The solid is characterized by proton NMR in deuterated DMSO, 500 MHz, Methanol, δ 0.91 (t, 3H); 1.29 (m, 24H); 1.64 (m, 2H); 2.39 (t, 2H); 2.75 (m, 2H); 3.21 (s, 9H); 3.71 (d, 1H); 3.87 (dd, 1H); 5.62 (m, 1H).

Example 7: Preparation of o-Palmitoyl-L-Carnitine Monohydrate

Ion exchange chromatography is used to remove chlorine from o-palmitoyl-L-carnitine HCl monohydrate through use of a cationic exchange resin charged with hydroxide ion. o-palmitoyl-L-carnitine HCl monohydrate is dissolved at 25 mg/mL in deionized water and put through a column of radius 0.75 cm and height of 6 cm at a flow rate of 5-10 mL/min. One fraction is collected as twice the volume added to the column and white precipitate will appear after minutes. The sample is then frozen and lyophilized, and is stored in a refrigerator or desiccator for subsequent use. The solid is characterized by proton NMR in deuterated DMSO, 500 MHz, Methanol, δ 0.90 (t, 3H); 1.29 (m, 24H); 1.63 (m, 2H); 2.37 (m, 2H); 2.61 (dd, 1H); 3.18 (s, 9H); 3.71 (m, 2H); 5.60 (m, 1H).

Figure 6:
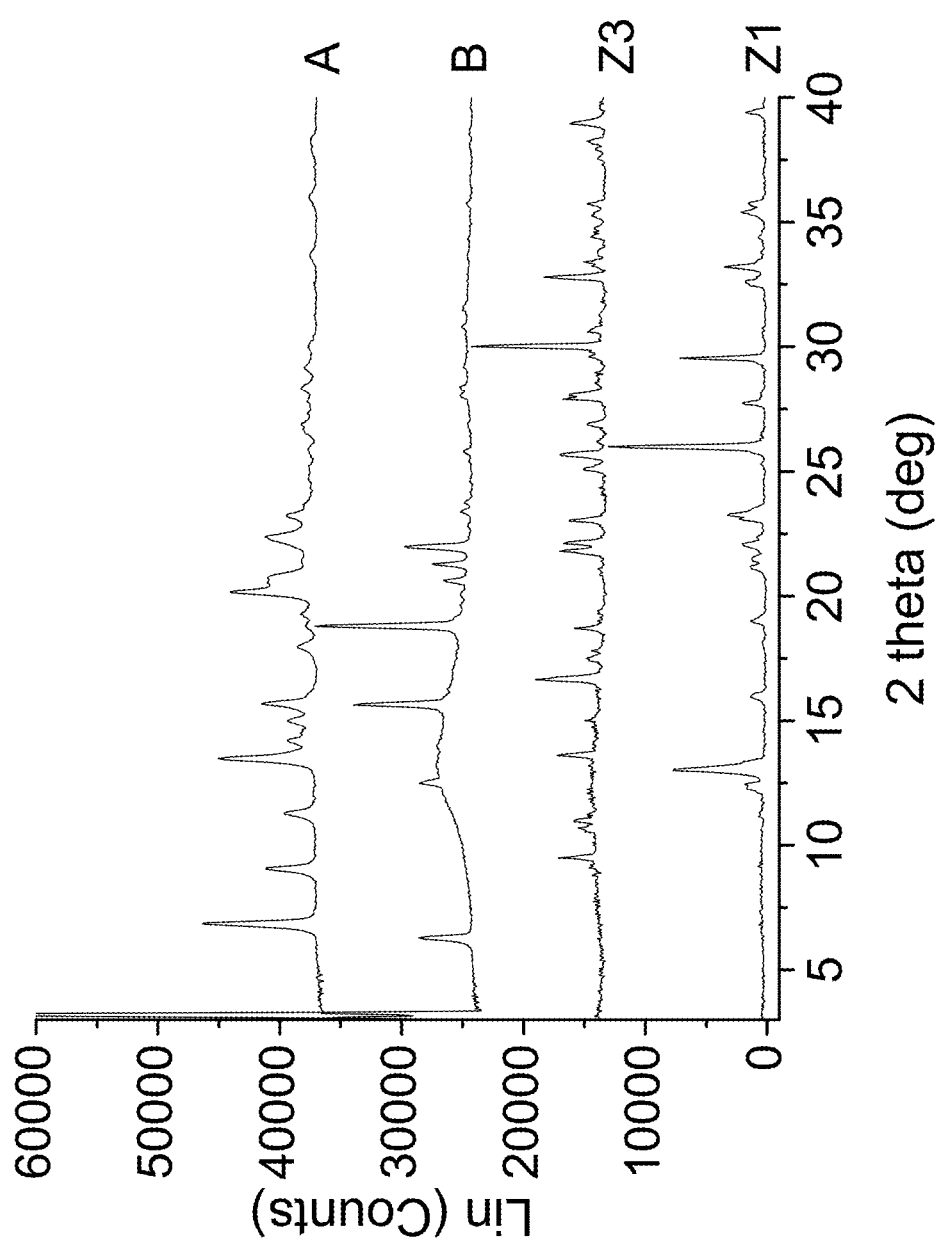
FIG. 6. PXRD diffractograms of; (A=zoledronic acid, o-palmitoyl-L-carnitine and water complex (1:1:1)). (B=o-palmitoyl-L-carnitine). (Z1=Zoledronic acid monohydrate). (Z3=Zoledronic acid trihydrate)
Figure 7:
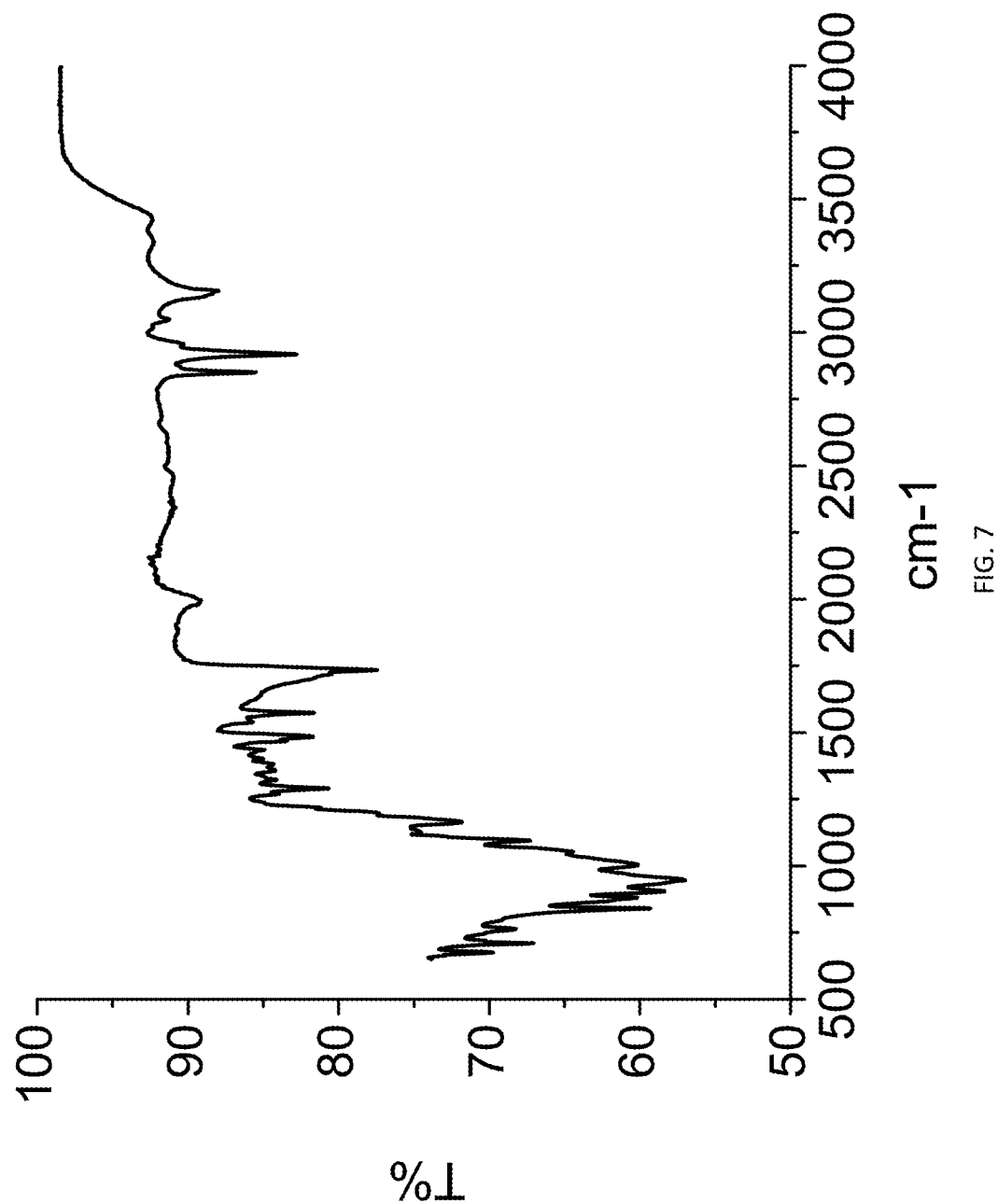
FIG. 7. FTIR spectrum of; a complex comprising zoledronic acid, o-palmitoyl-L-carnitine, and water (1:1:1).

Example 8: Preparation of Zoledronic Acid, o-Palmitoyl-L-Carnitine and Water Complex (1:1:1) by Solvent-Drop Grinding 100 mg of zoledronic acid was ground with 137.8 mg of o-palmitoyl-L-carnitine and 40 μl of water or methanol was added to the solid mixture. The solids gathered after grinding were stored in screw cap vials for subsequent analysis. The material was characterized by PXRD and FTIR corresponding to FIGS. 6 and 7, respectively.

Example 9: Preparation of Zoledronic Acid, o-Palmitoyl-L-Carnitine and Water Complex (1:1:1) by Slurry 158 mg of zoledronic acid and 237 mg of o-palmitoyl-L-carnitine were slurried in 2 ml of water overnight. The solids gathered after filtration were dried and stored in a screw cap vials for subsequent analysis.

Figure 8:
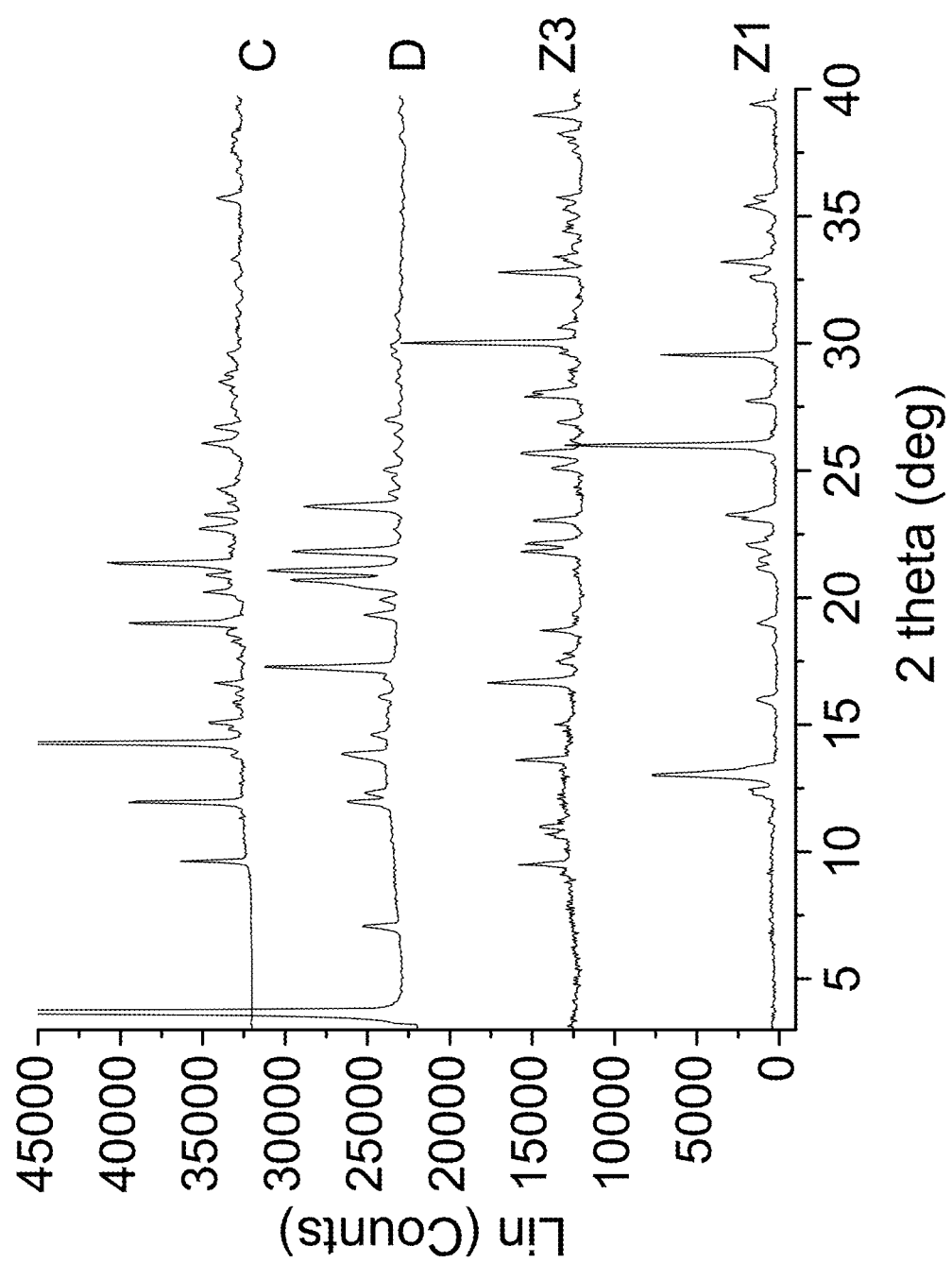
FIG. 8. PXRD diffractograms of; (C=zoledronic acid, o-myristoyl-L-carnitine and water complex (1:1:1)). (D=o-myristoyl-L-carnitine). (Z1=Zoledronic acid monohydrate). (Z3=Zoledronic acid trihydrate)
Figure 9:
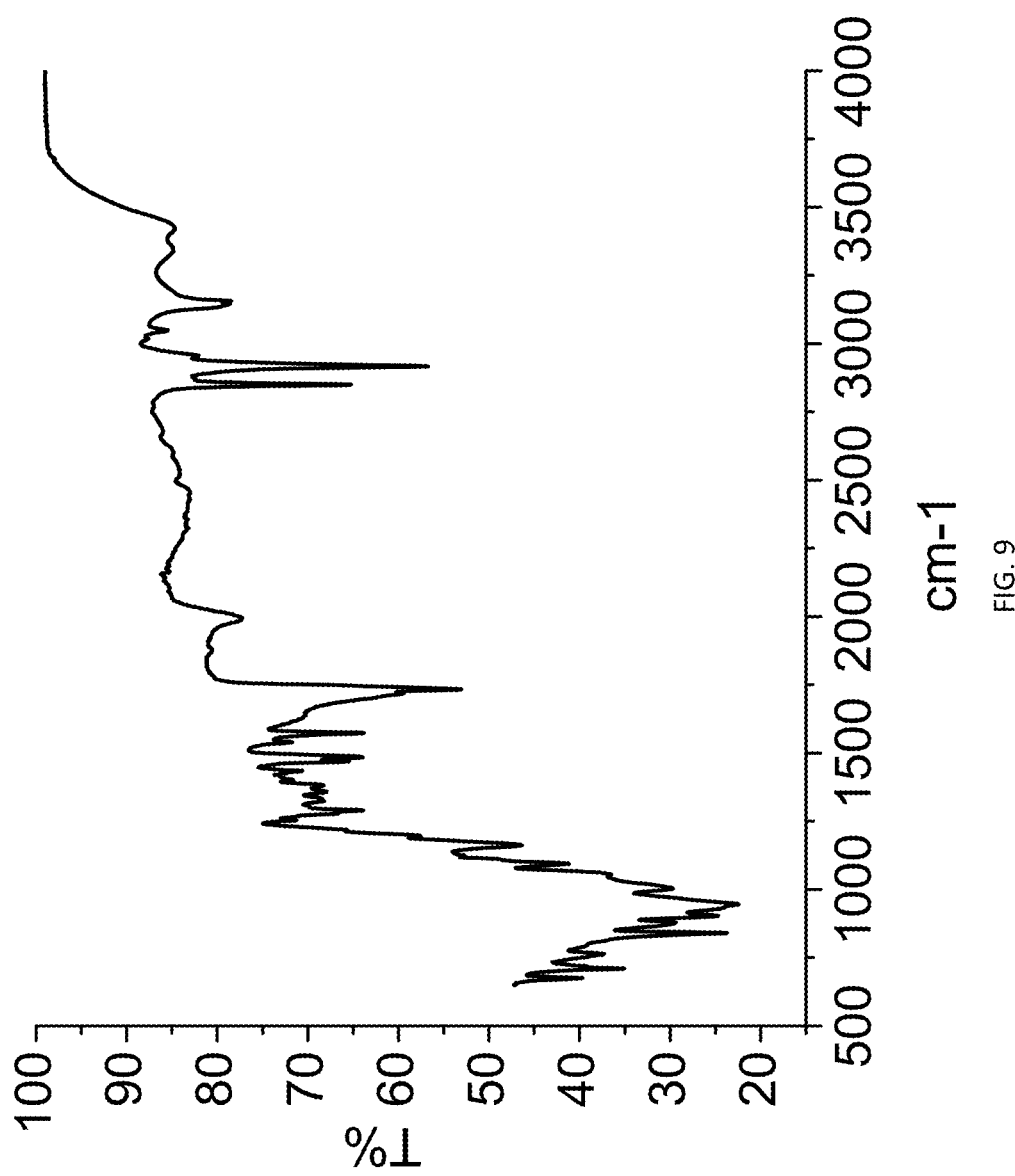
FIG. 9. FTIR spectrum of; a complex comprising zoledronic acid, o-myristoyl-L-carnitine, and water (1:1:1).

Example 10: Preparation of Zoledronic Acid, o-Myristoyl-L-Carnitine and Water Complex (1:1:1) by Slurry 160 mg of zoledronic acid and 205 mg of o-myristoyl-L-carnitine were slurried in 2 ml of water overnight. The solids gathered after filtration were dried and stored in a screw cap vials for subsequent analysis. The material was characterized by PXRD and FTIR corresponding to FIGS. 8 and 9 respectively.

Figure 10:
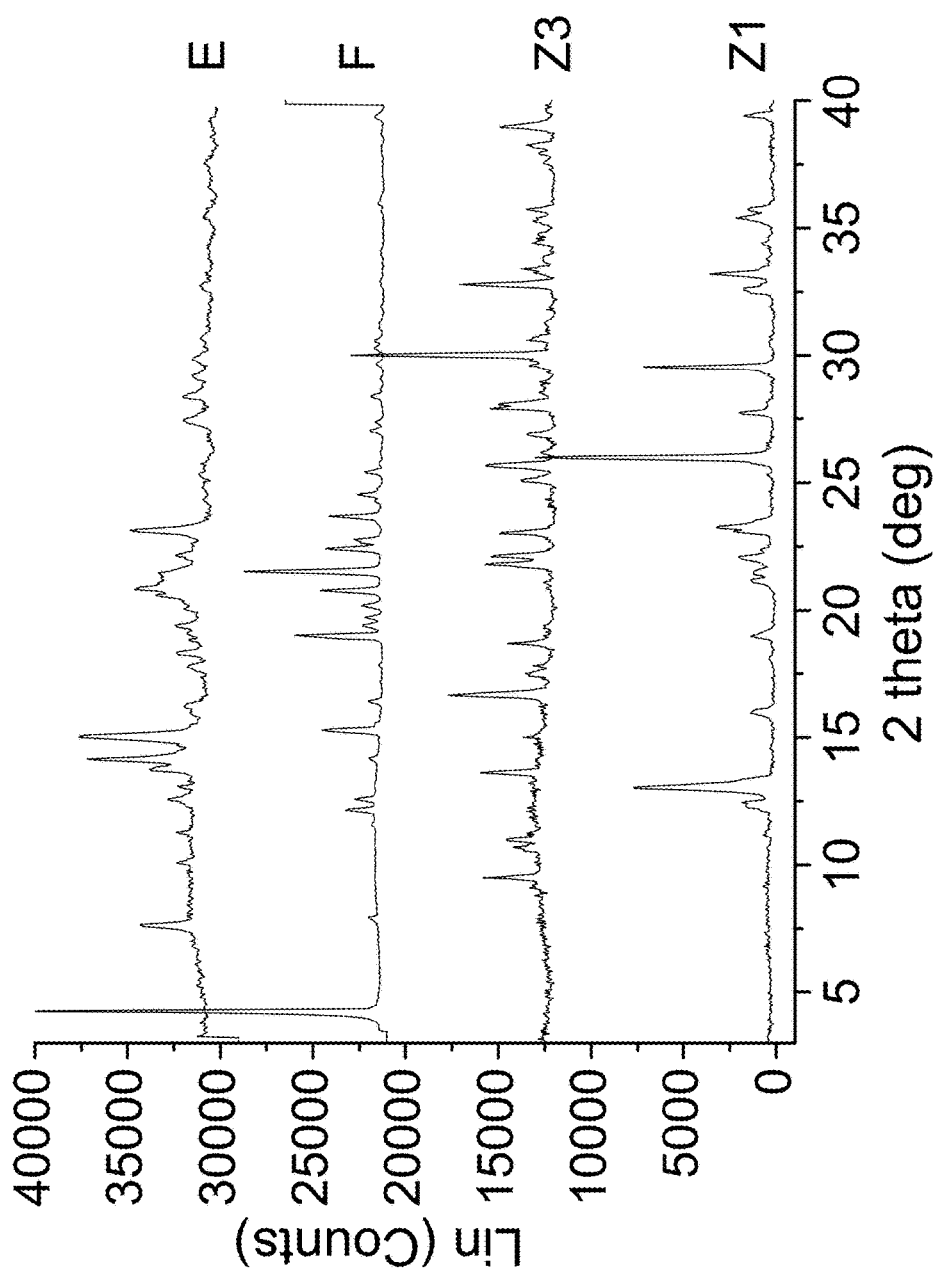
FIG. 10. PXRD diffractograms of; (E=zoledronic acid, o-lauroyl-L-carnitine, and water complex (1:1:1)). (F=o-lauroyl-L-carnitine). (Z1=Zoledronic acid monohydrate). (Z3=Zoledronic acid trihydrate)
Figure 11:
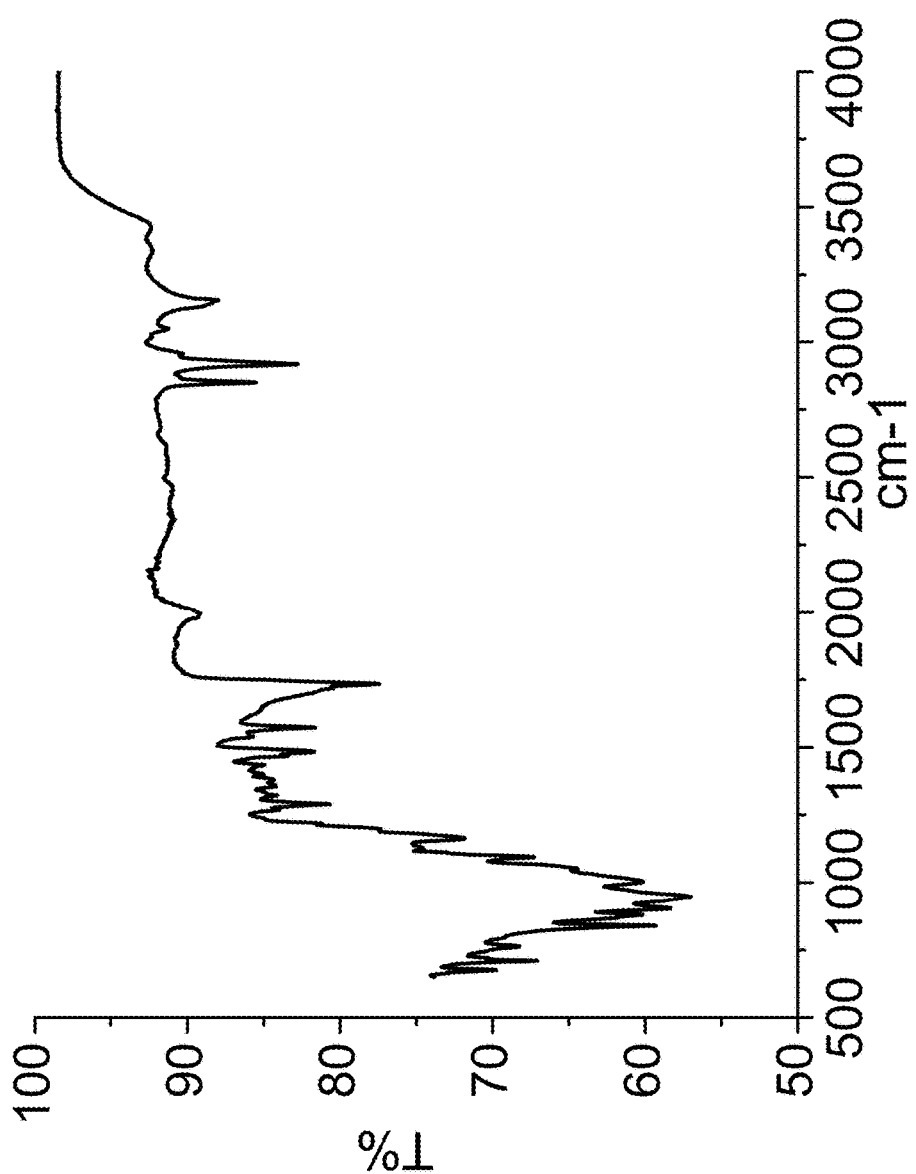
FIG. 11. FTIR spectrum of zoledronic acid, o-lauroyl-L-carnitine, and water complex (1:1:1).

Example 11: Preparation of Zoledronic Acid, o-Lauroyl-L-Carnitine and Water Complex (1:1:1) by Slurry 180 mg of zoledronic acid and 213 mg of o-lauroyl-L-carnitine were slurried in 2 ml of methanol overnight. The solids gathered after filtration were dried and stored in a screw cap vials for subsequent analysis. The material was characterized by PXRD and FTIR corresponding to FIGS. 10 and 11 respectively.

Figure 12:
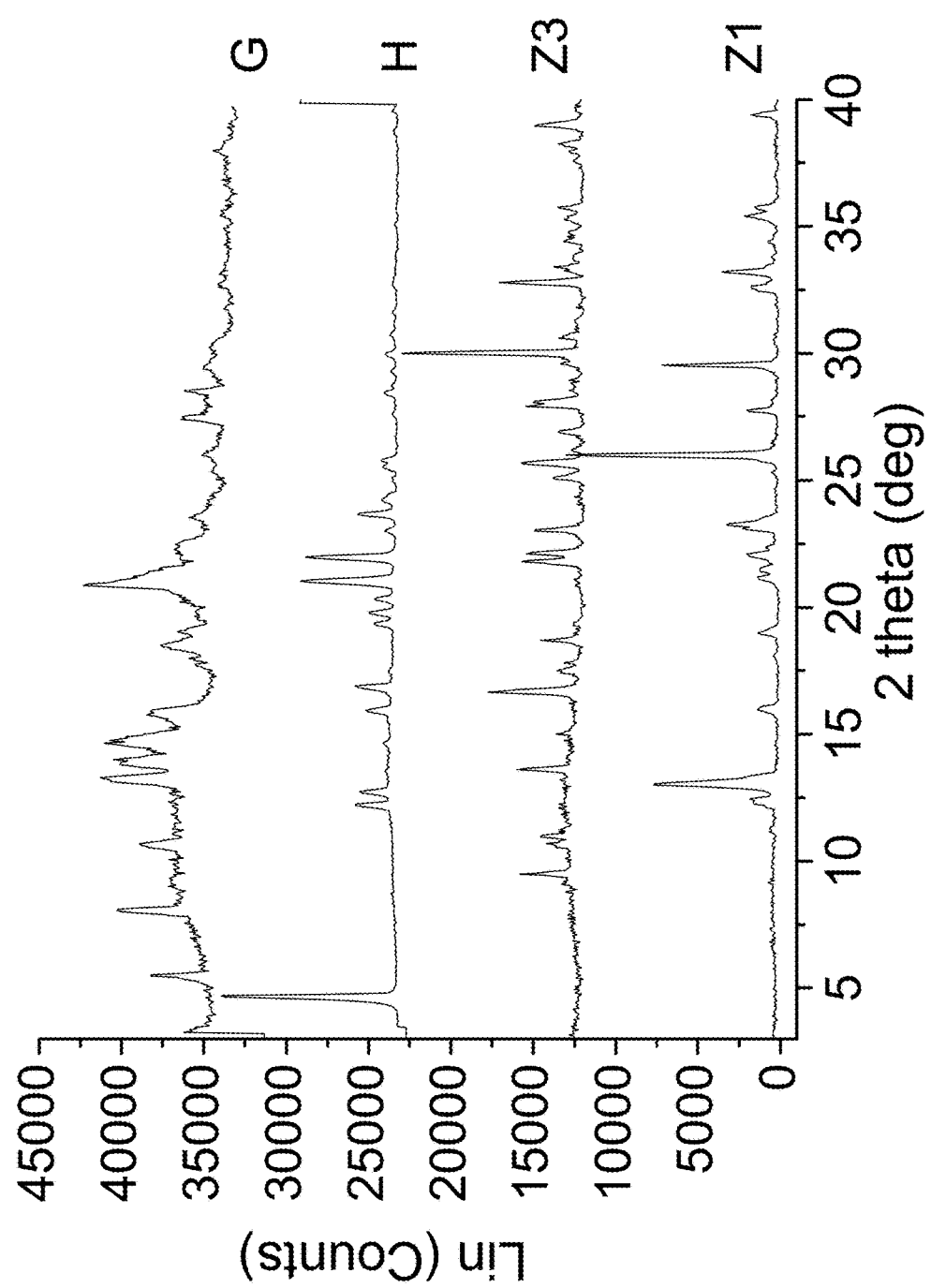
FIG. 12. PXRD diffractograms of; (G=zoledronic acid, o-decanoyl-L-carnitine, and water complex (1:1:1)). (H=o-decanoyl-L-carnitine). (Z1=Zoledronic acid monohydrate). (Z3=Zoledronic acid trihydrate)
Figure 13:
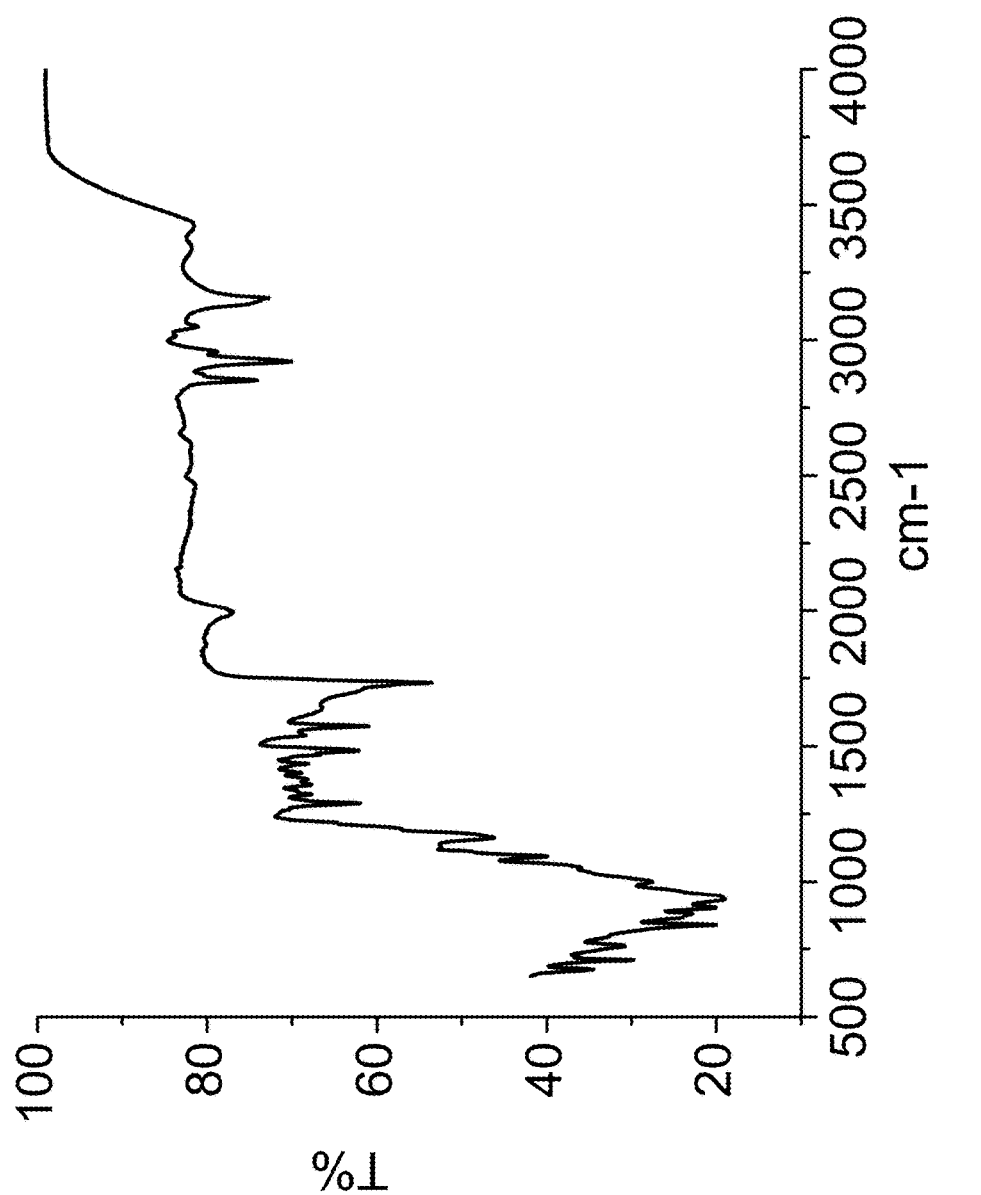
FIG. 13. FTIR spectrum of zoledronic acid, o-decanoyl-L-carnitine, and water complex (1:1:1).

Example 12: Preparation of Zoledronic Acid, o-Decanoyl-L-Carnitine and Water Complex (1:1:1) by Slurry 200 mg of zoledronic acid and 218 mg of o-decanoyl-L-carnitine were slurried in 2 ml of methanol overnight. The solids gathered after filtration were dried and stored in a screw cap vials for subsequent analysis. The material was characterized by PXRD and FTIR corresponding to FIGS. 12 and 13 respectively.

Figure 14:
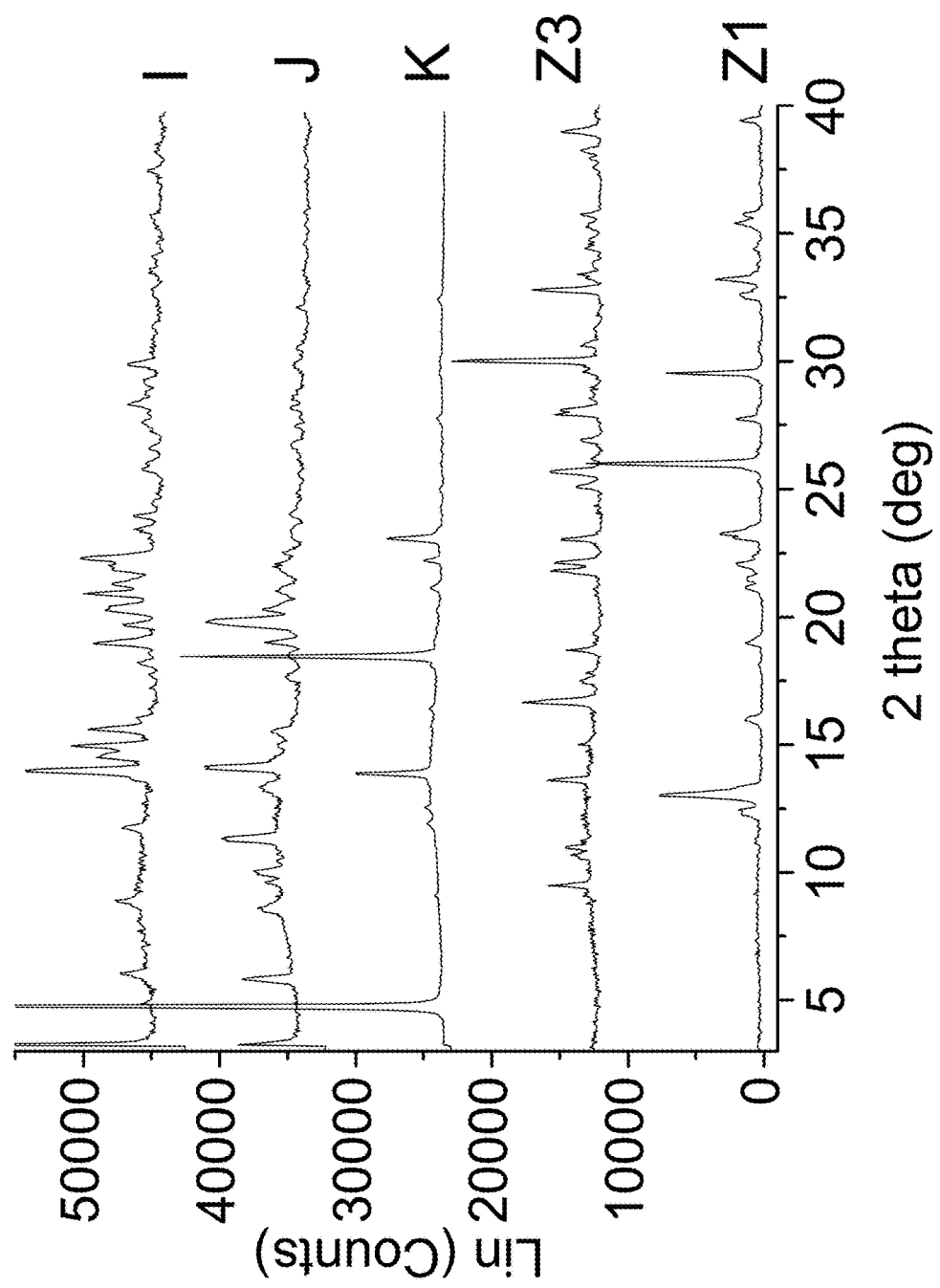
FIG. 14. PXRD diffractograms of; (I=zoledronic acid, o-octanoyl-L-carnitine, and water complex (1:1:1)). (J=o-octanoyl-L-carnitine). (K=zoledronic acid, o-octanoyl-L-carnitine, and water complex (1:1:1.5) (Z1=Zoledronic acid monohydrate). (Z3=Zoledronic acid trihydrate)
Figure 15:
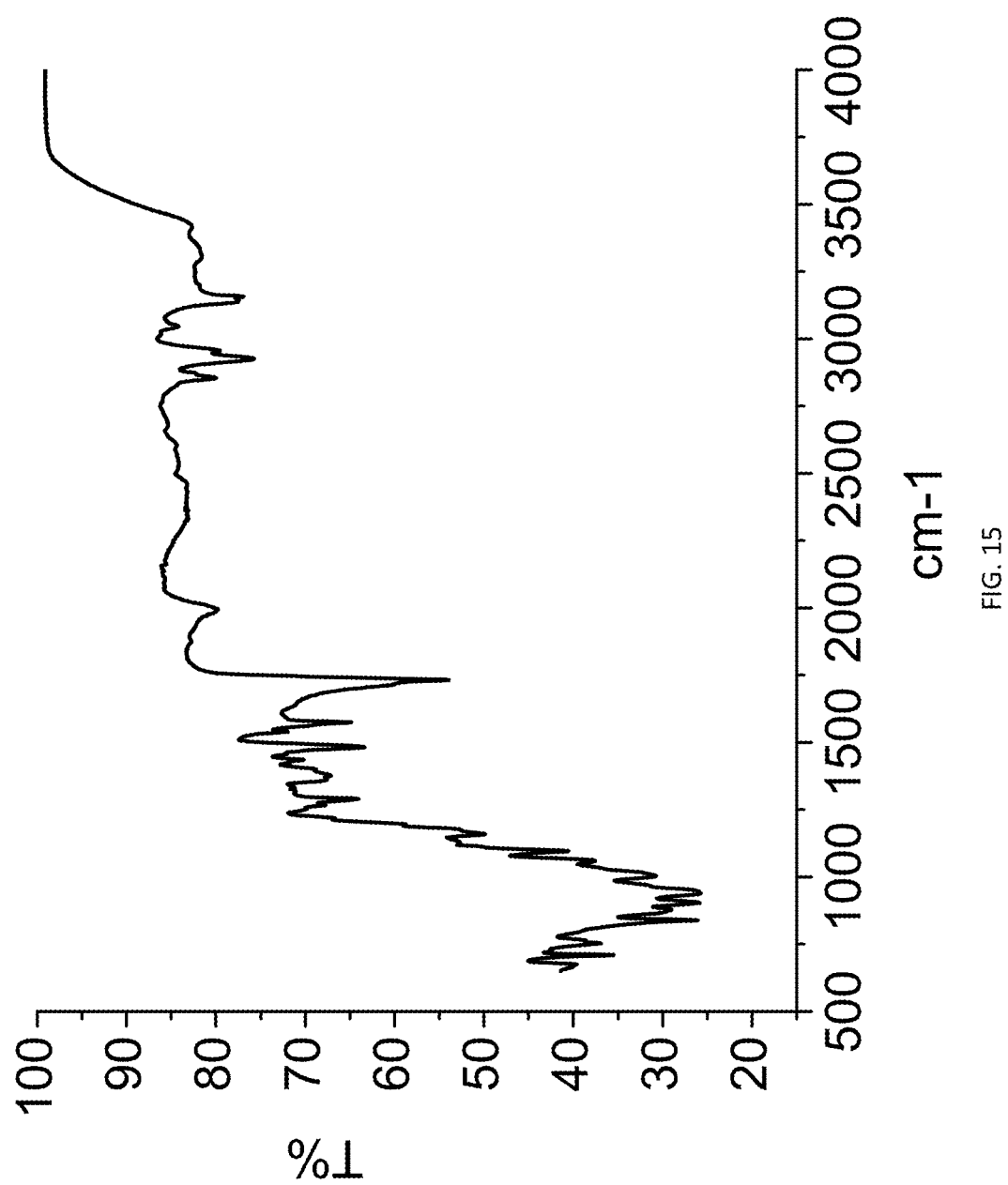
FIG. 15. FTIR spectrum of zoledronic acid, zoledronic, o-octanoyl-L-carnitine, and water complex (1:1:1).

Example 13: Preparation of Zoledronic Acid, o-Octanoyl-L-Carnitine and Water Complex (1:1:1) by Slurry 200 mg of zoledronic acid and 198 mg of o-octanoyl-L-carnitine were slurried in 2 ml of methanol overnight. The solids gathered after filtration were dried and stored in a screw cap vials for subsequent analysis. The material was characterized by PXRD and FTIR corresponding to FIGS. 14J and 15 respectively.

Figure 16:
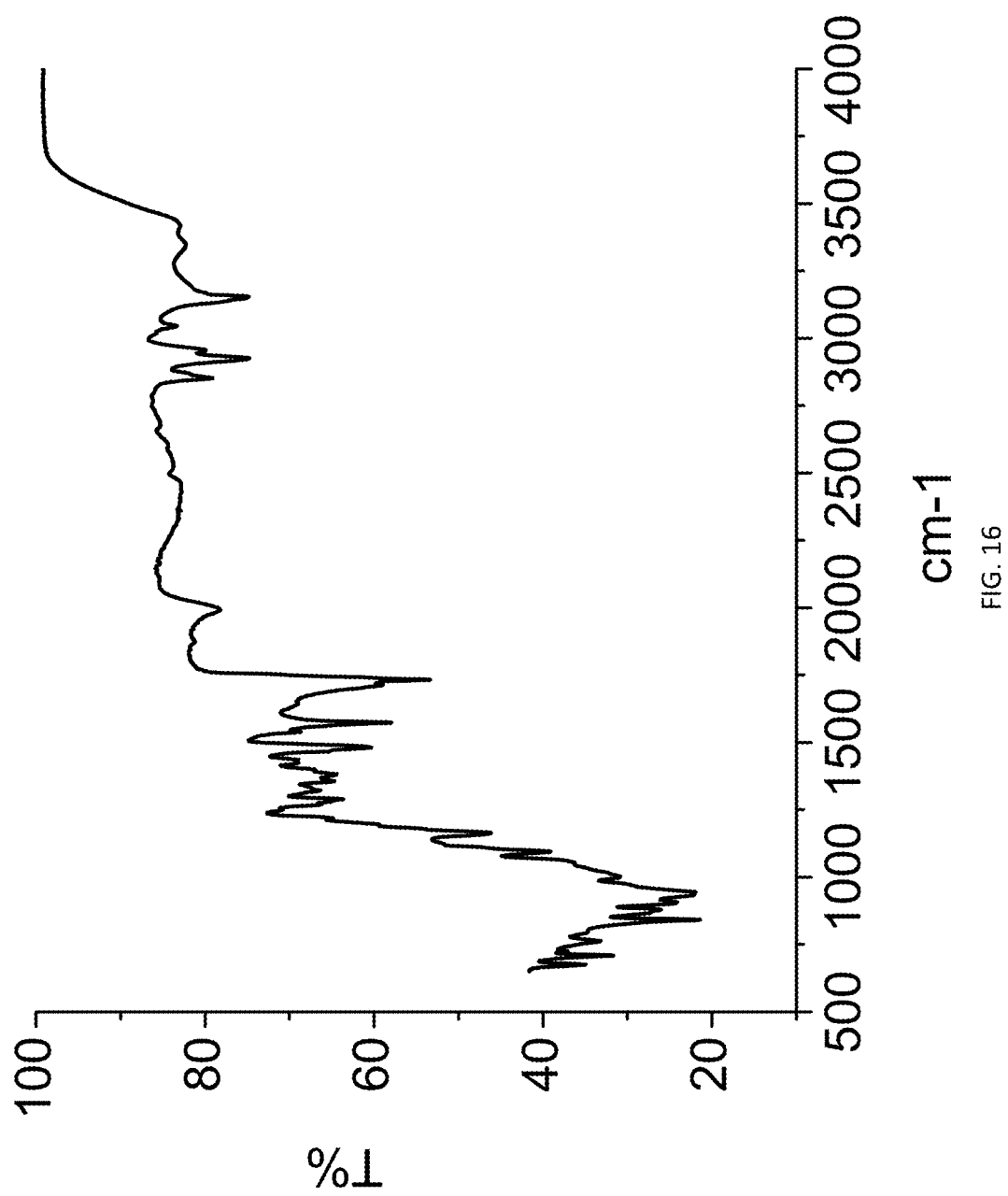
FIG. 16. FTIR spectrum of zoledronic acid, o-octanoyl-L-carnitine, and water complex (1:1:1.5).
Figure 17:
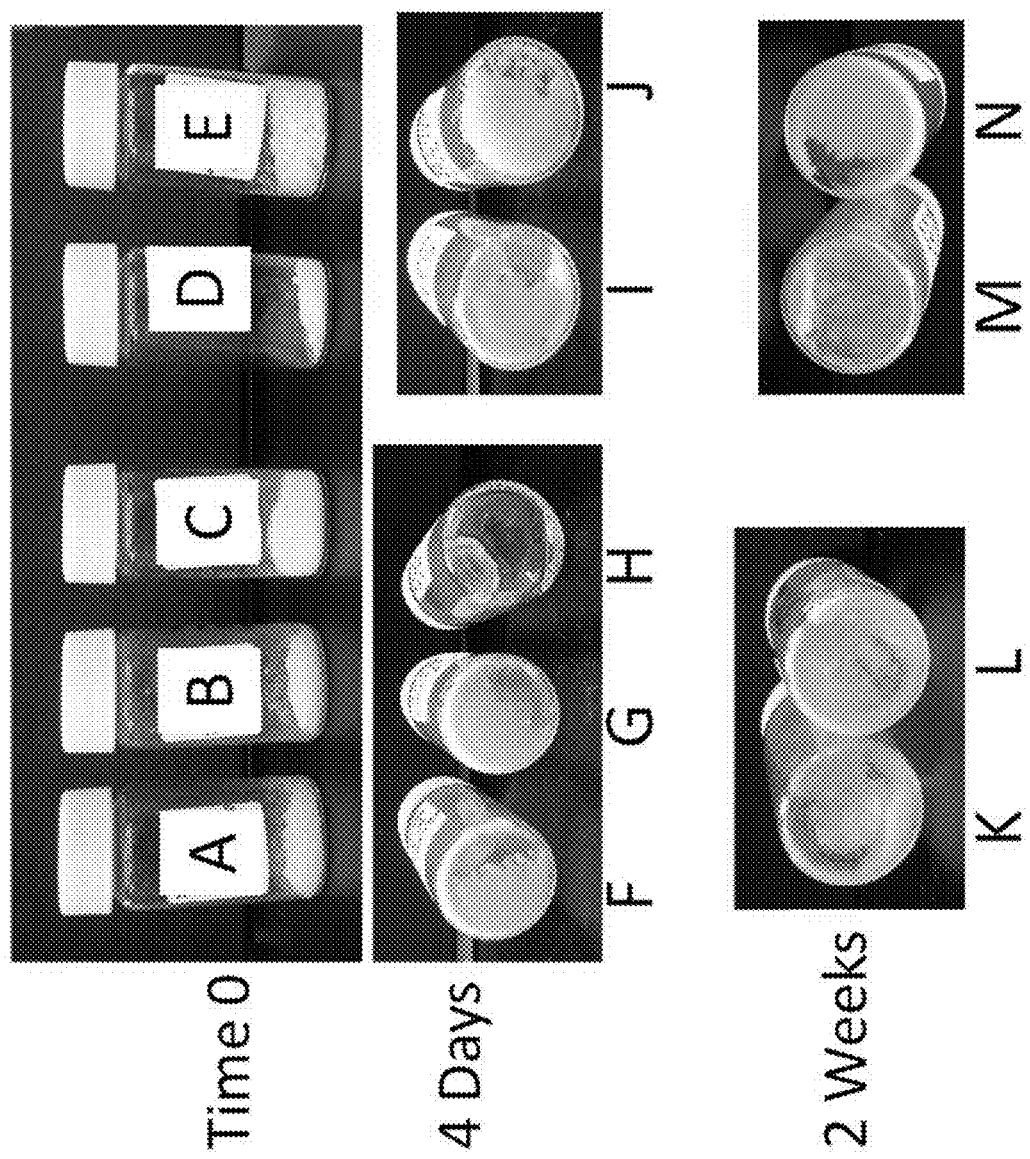
FIG. 17. Accelerated Stability: 40° C./75% Relative Humidity for C8-C10 carnitine complexes with ZA. A=ZA:C8carn monohydrate, B=ZA:C8carn sesquihydrate, C=o-octanoyl-L-carnitine monohydrate, D=ZA:C10carn monohydrate, E=o-decanoyl-L-carnitine monohydrate, F=ZA:C8carn monohydrate, G=ZA:C8carn sesquihydrate, H=o-octanoyl-L-carnitine monohydrate, I=ZA:C10carn monohydrate, J=o-decanoyl-L-carnitine monohydrate, K=ZA:C8carn monohydrate, L=ZA:C8carn sesquihydrate, M=ZA:C10carn monohydrate, and N=o-decanoyl-L-carnitine monohydrate.
Figure 18:
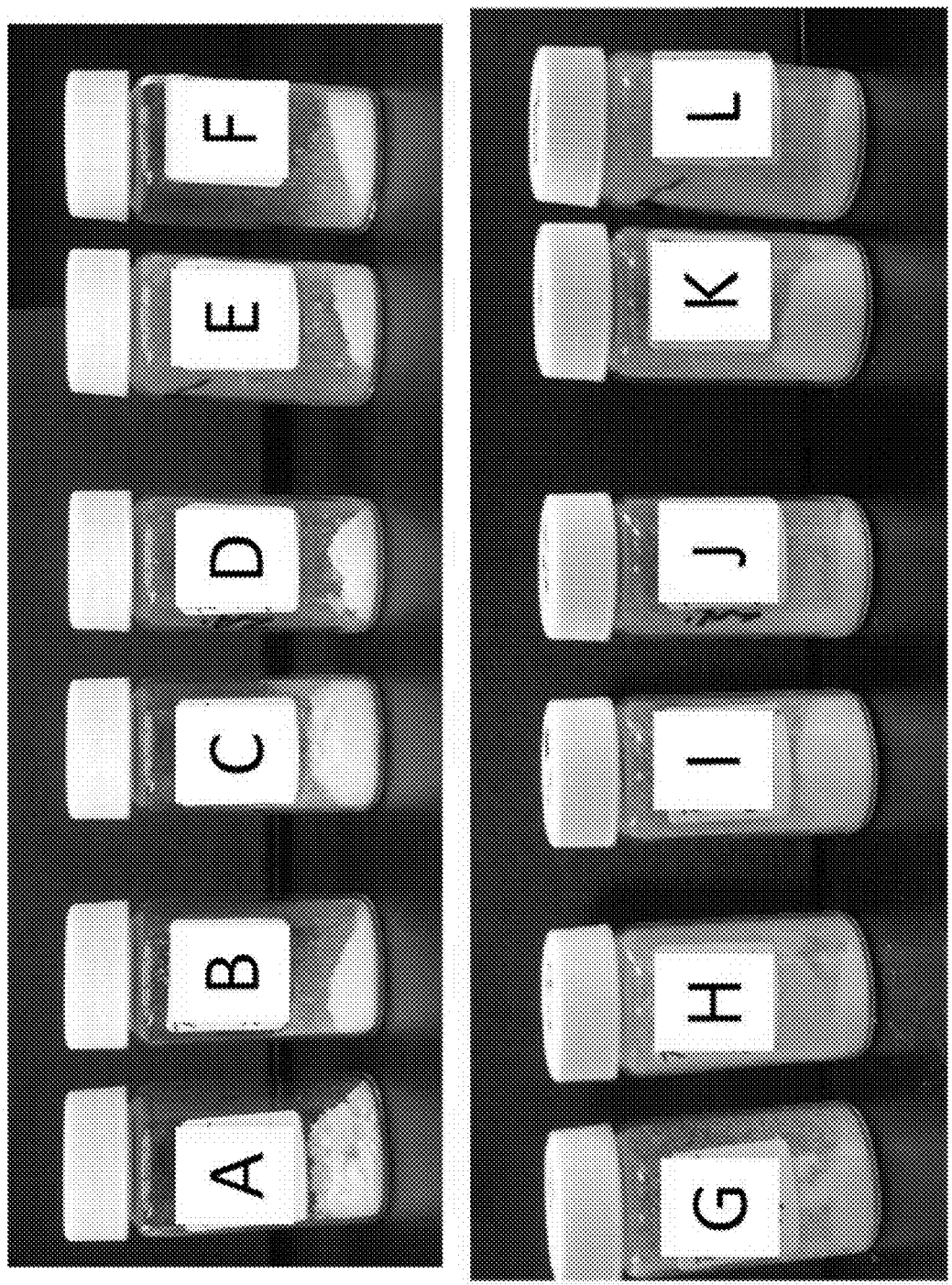
FIG. 18. Accelerated Stability: 40° C./75% Relative Humidity for C12-C14 carnitine complexes with ZA. Time zero; A=o-lauroyl-L-carnitine monohydrate, B=ZA:C12 carnitine monohydrate, C=o-myristoyl-L-carnitine monohydrate, D=ZA:C14carn monohydrate, E=ZA:C16carn monohydrate, and F=o-palmitoyl-L-carnitine monohydrate. Two weeks; G=o-lauroyl-L-carnitine monohydrate, H=ZA:C12 carnitine monohydrate, I=o-myristoyl-L-carnitine monohydrate, J=ZA:C14carn monohydrate, K=o-palmitoyl-L-carnitine monohydrate, and L=ZA:C16carn monohydrate.
Figure 19:
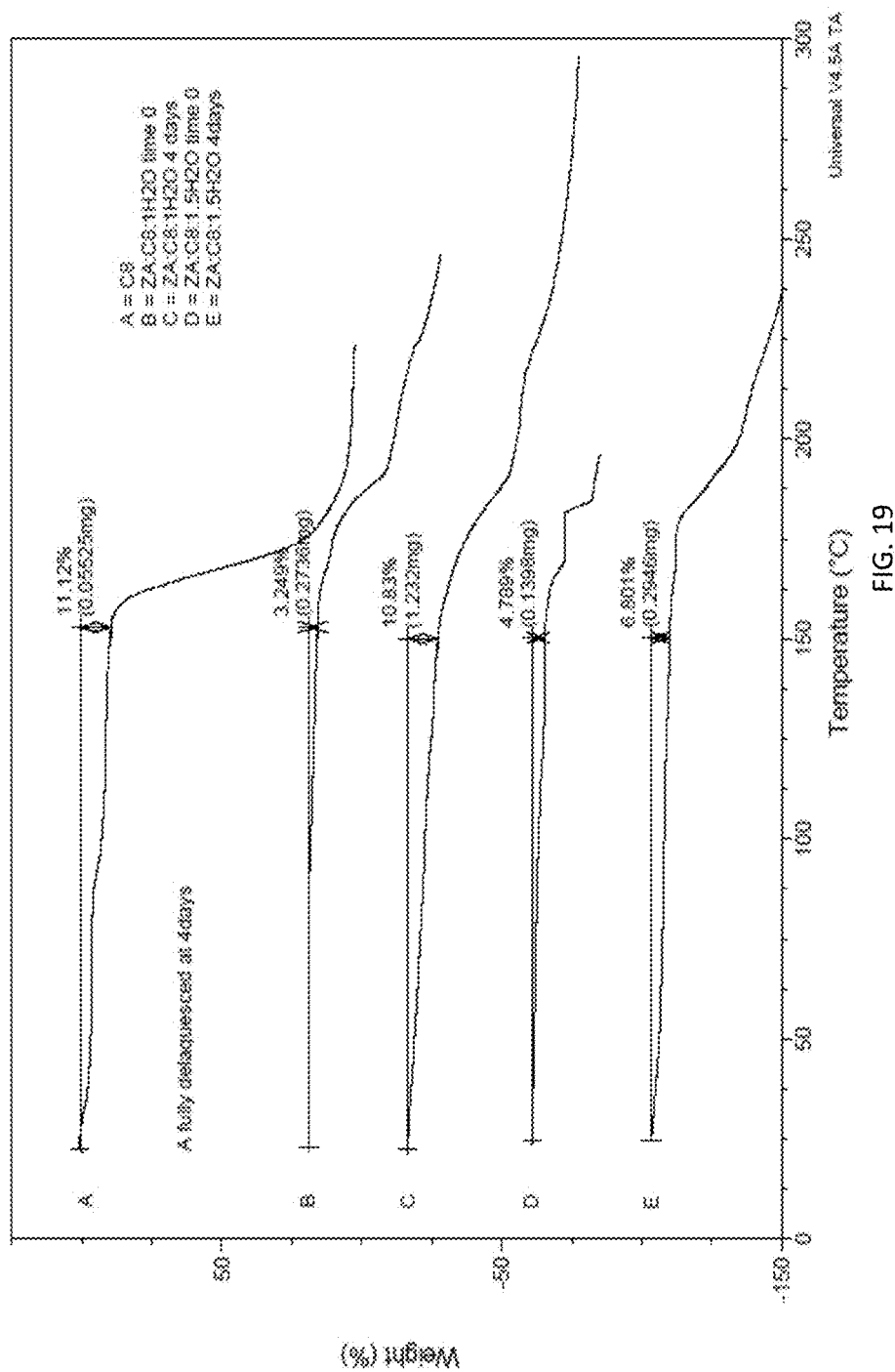
FIG. 19. TGA data for; o-octanoyl-L-carnitine monohydrate and corresponding complexes with ZA.
Figure 20:
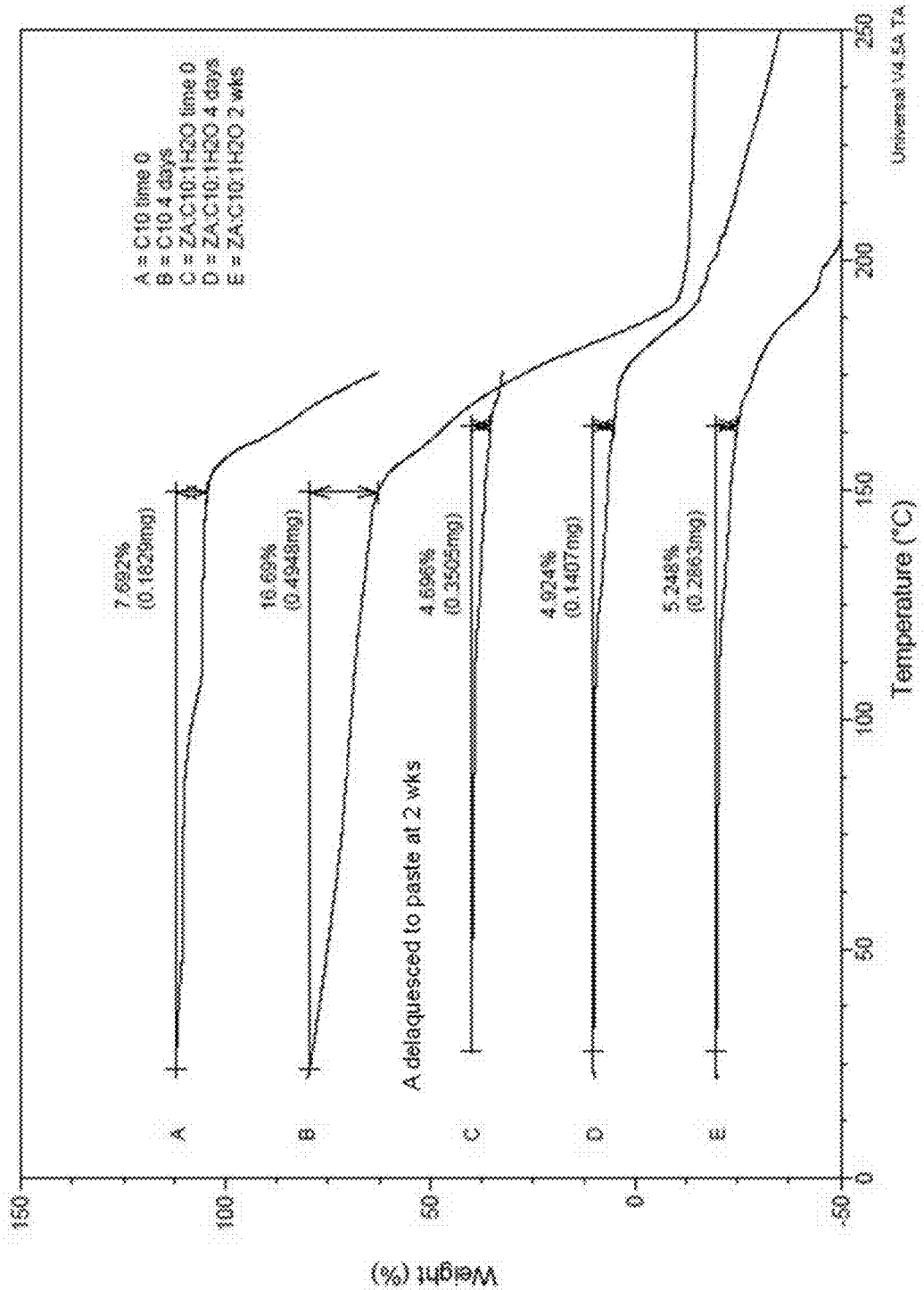
FIG. 20. TGA data for; o-decanoyl-L-carnitine monohydrate and corresponding complexes with ZA.
Figure 21:
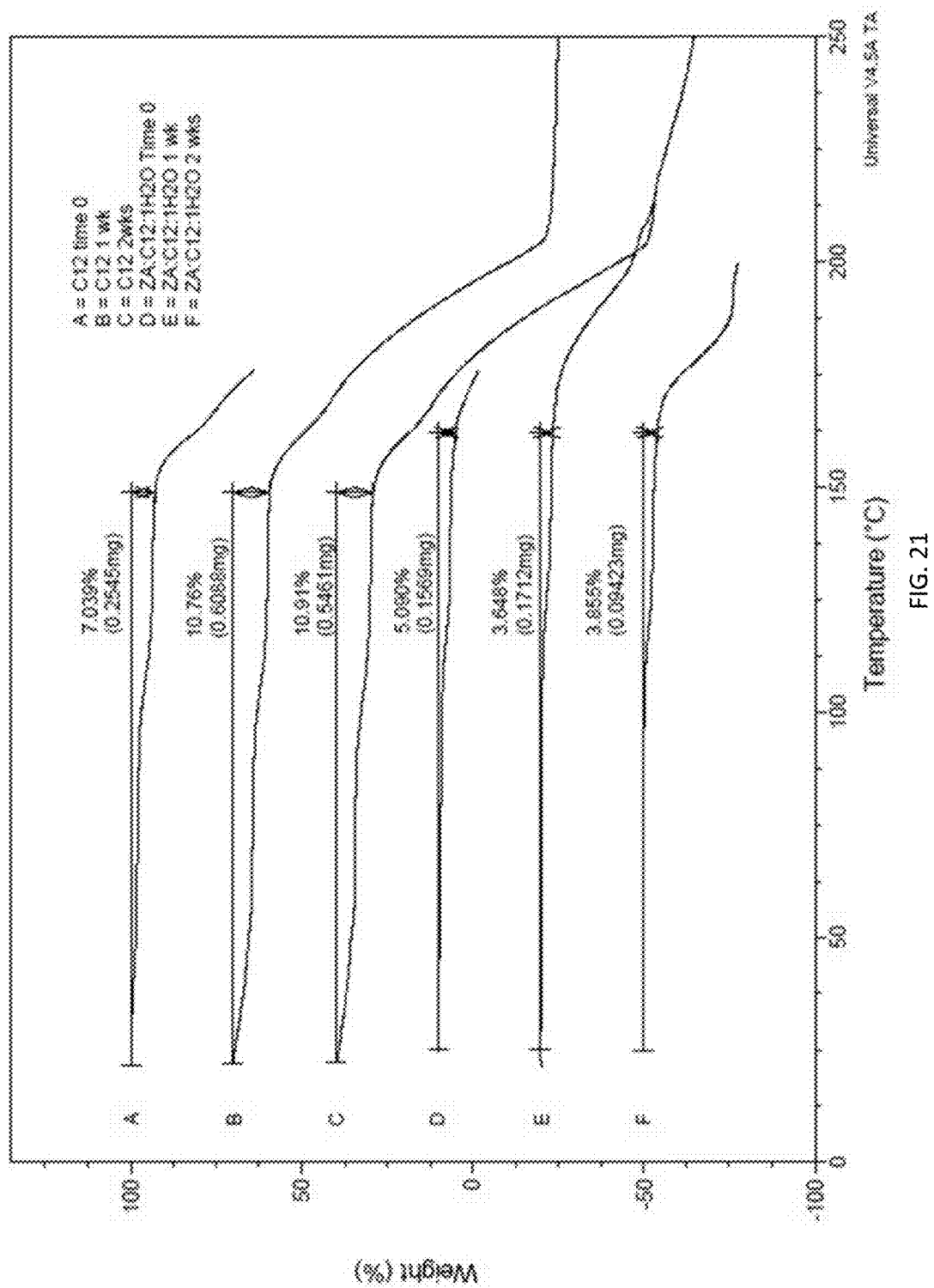
FIG. 21. Accelerated TGA data for; o-lauroyl-L-carnitine monohydrate and corresponding complexes with ZA.
Figure 22:
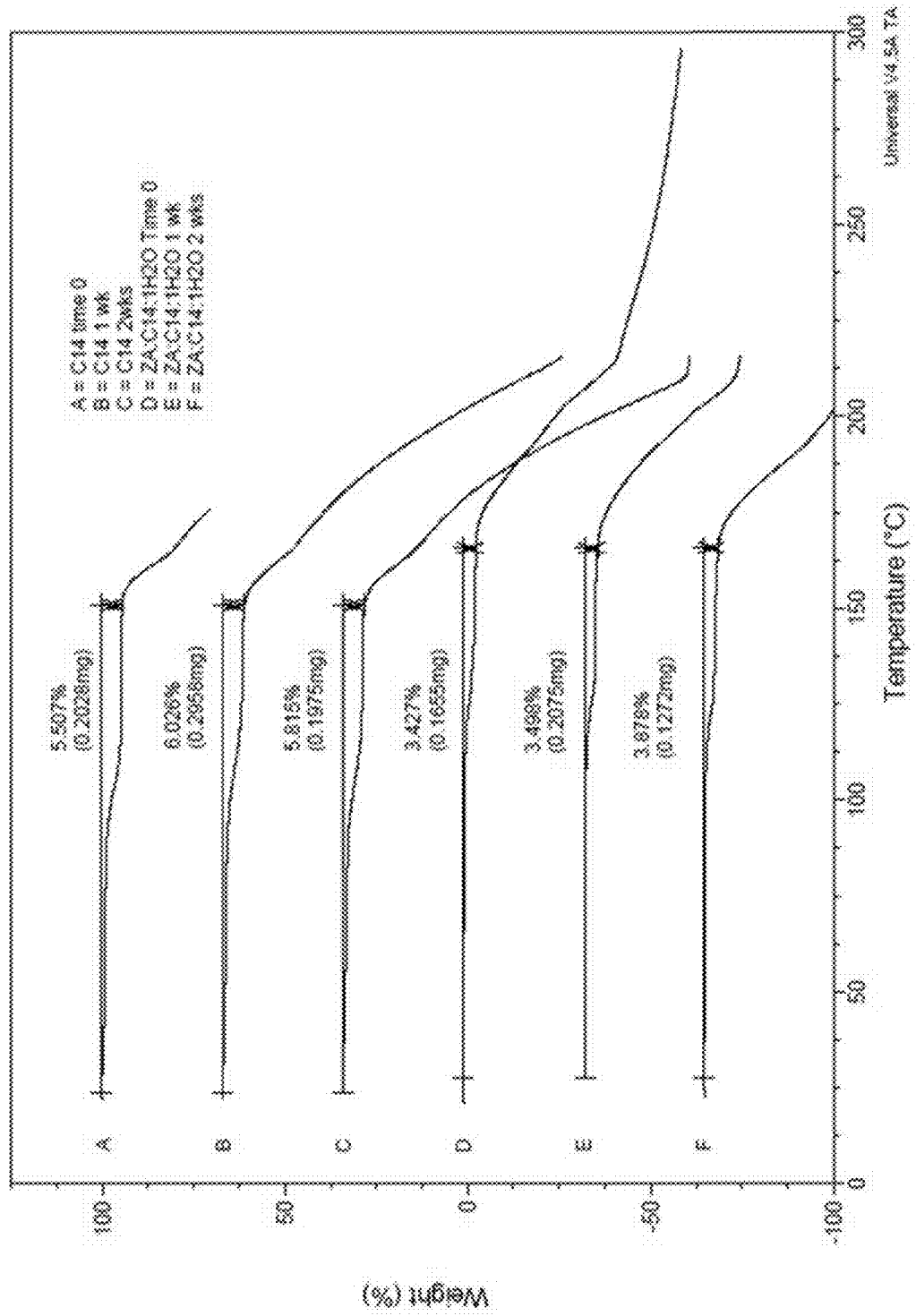
FIG. 22. Accelerated TGA data for; o-myristoyl-L-carnitine monohydrate and corresponding complexes with ZA.
Figure 23:
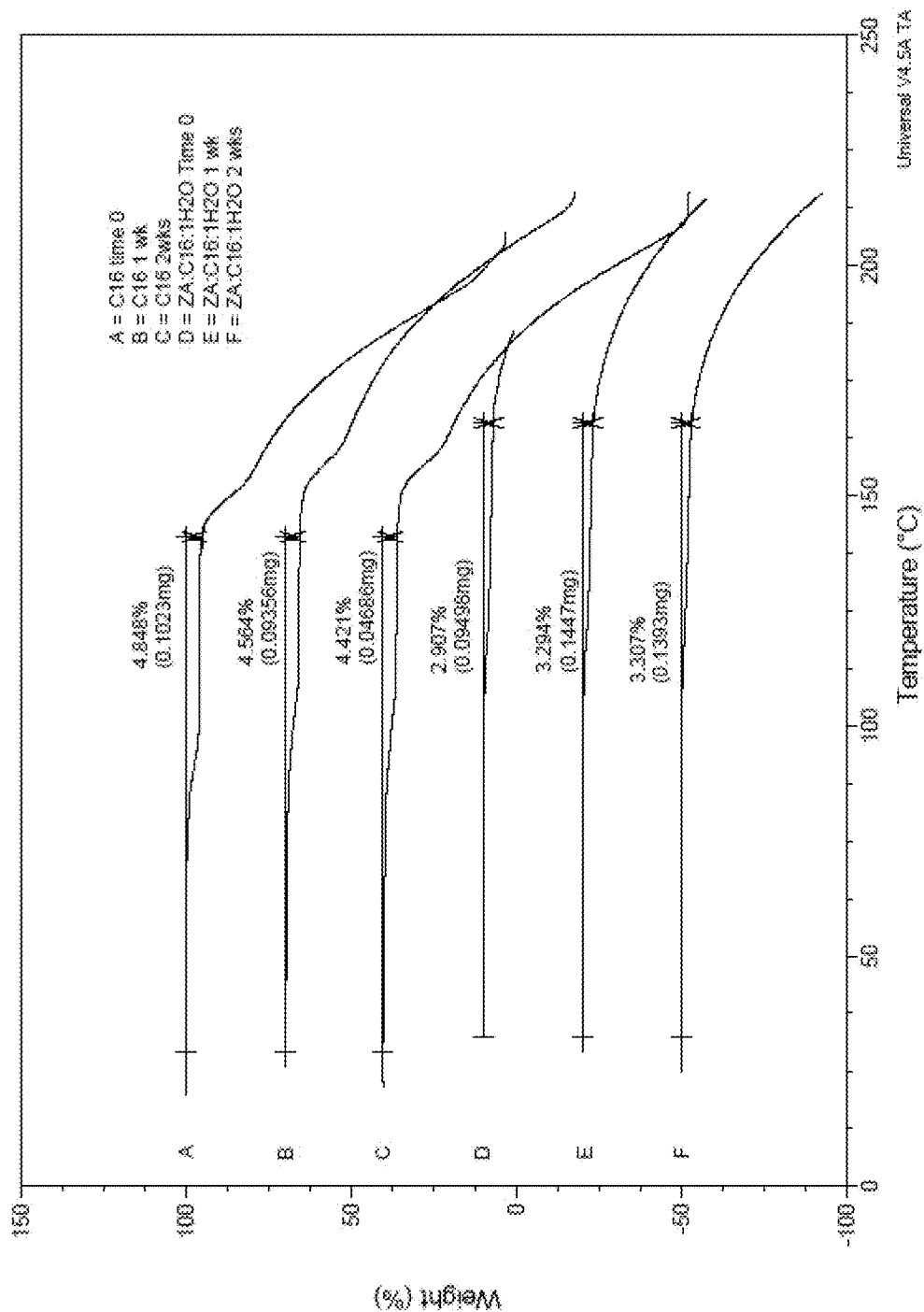
FIG. 23. Accelerated TGA data for; o-palmitoyl-L-carnitine monohydrate and corresponding complexes with ZA.

Example 14: Preparation of Zoledronic Acid, o-Octanoyl-L-Carnitine and Water Complex (1:1:1.5) by Slurry 200 mg of zoledronic acid and 198 mg of o-octanoyl-L-carnitine were dissolved in 2 ml of water, frozen and lyophilized. The solids gathered after lyophilization were characterized by PXRD and FTIR corresponding to FIGS. 14K and 16 respectively.

Example 15: Accelerated Stability of Zoledronic Acid, o-Palmitoyl-L-Carnitine and Water Complex (1:1:1)

500 mg of zoledronic acid, o-palmitoyl-L-carnitine and water complex (1:1:1) is placed into an open vial and placed into a closed chamber exhibiting 75% relative humidity via a saturated sodium chloride solution inside the chamber which is at 40° C. for two weeks. The material was characterized by visual analysis and TGA exemplified in FIGS. 17-23.

The claimed invention is:

1. A crystalline form of zoledronic acid selected from the group consisting of:
    a zoledronic acid L-carnitine hydrated complex,
    a zoledronic acid L-carnitine complex,
    a zoledronic acid, o-palmitoyl-L-carnitine and water complex (1:1:1),
    a zoledronic acid, o-myristoyl-L-carnitine and water complex (1:1:1),
    a zoledronic acid, o-lauroyl-L-carnitine, and water complex (1:1:1),
    a zoledronic acid, o-decanoyl-L-carnitine, and water complex (1:1:1),
    a zoledronic acid, o-octanoyl-L-carnitine, and water complex (1:1:1),
    a zoledronic acid, o-octanoyl-L-carnitine, and water complex (1:1:1.5), and
    a zoledronic, L-carnitine, and water complex (1:1:1).

2. A crystalline form of zoledronic acid according to claim 1 selected from the group consisting of:
    a zoledronic acid L-carnitine hydrated complex, characterized by a PXRD pattern having strong peaks at about 7.3, 12.6, 15.7, 17.8, 27.5±0.2 degrees two-theta;
    a zoledronic acid L-carnitine complex, characterized by a PXRD pattern having peaks at about 8.8, 9.6, 13.2, 19.0, 30.4±0.2 degrees two-theta;
    a zoledronic acid, o-palmitoyl-L-carnitine and water complex (1:1:1), characterized by a PXRD pattern having strong peaks at about 6.8, 9.0, 13.5, 20.2, and 22.4±0.2 degrees two-theta;
    a zoledronic acid, o-myristoyl-L-carnitine and water complex (1:1:1), characterized by a PXRD pattern having strong peaks at about 9.6, 11.9, 14.3, 19.0, and 21.4±0.2 degrees two-theta;
    a zoledronic acid, o-lauroyl-L-carnitine, and water complex (1:1:1), characterized by a PXRD pattern having strong peaks at about 7.6, 14.1, 14.9, 20.8, and 23.1±0.2 degrees two-theta;
    a zoledronic acid, o-decanoyl-L-carnitine, and water complex (1:1:1), characterized by a PXRD pattern having strong peaks at about 5.5, 8.1, 13.3, 18.5, and 20.9±0.2 degrees two-theta;
    a zoledronic acid, o-octanoyl-L-carnitine, and water complex (1:1:1), characterized by a PXRD pattern having strong peaks at about 3.25, 5.8, 11.3, 14.1, and 19.8±0.2 degrees two-theta;
    a zoledronic acid, o-octanoyl-L-carnitine, and water complex (1:1:1.5), characterized by a PXRD pattern having strong peaks at about 3.3, 6.1, 14.0, 15.0, and 20.9±0.2 degrees two-theta; and
    a zoledronic, L-carnitine, and water complex (1:1:1), characterized by a PXRD pattern having strong peaks at about 9.6, 10.0, 13.2, 18.9, 19.9±0.2 degrees two-theta.

3. A pharmaceutical formulation comprising a crystalline form of zoledronic acid selected from the group consisting of:
    a zoledronic acid L-carnitine hydrated complex,
    a zoledronic acid L-carnitine complex,
    a zoledronic acid, o-palmitoyl-L-carnitine and water complex (1:1:1),
    a zoledronic acid, o-myristoyl-L-carnitine and water complex (1:1:1),
    a zoledronic acid, o-lauroyl-L-carnitine, and water complex (1:1:1),
    a zoledronic acid, o-decanoyl-L-carnitine, and water complex (1:1:1),
    a zoledronic acid, o-octanoyl-L-carnitine, and water complex (1:1:1),
    a zoledronic acid, o-octanoyl-L-carnitine, and water complex (1:1:1.5), and
    a zoledronic, L-carnitine, and water complex (1:1:1) and at least one pharmaceutically acceptable carrier.

4. A pharmaceutical formulation according to claim 3, wherein the pharmaceutical formulation is an oral formulation.

5. A method of treating osteoporosis, tumor induced hypercalcemia (TIH), cancer-induced bone metastasis, or Paget's disease or for adjuvant or neoadjuvant therapies comprising the step of:
    administering to a patient in need thereof a therapeutically effective amount of a crystalline form of zoledronic acid according to claim 1.

6. A method of treating osteoporosis, tumor induced hypercalcemia (TIH), cancer-induced bone metastasis, or Paget's disease or for adjuvant or neoadjuvant therapies comprising the step of:
    administering to a patient in need thereof a therapeutically effective amount of a pharmaceutical formulation according to claim 3.

7. A method according to claim 5, wherein the administering step is oral administration.

8. A method according to claim 6, wherein the administering step is oral administration.

9. A method for preparing a crystalline form of zoledronic acid selected from the group consisting of:
    a zoledronic acid L-carnitine hydrated complex,
    a zoledronic acid L-carnitine complex,
    a zoledronic acid, o-palmitoyl-L-carnitine and water complex (1:1:1),
    a zoledronic acid, o-myristoyl-L-carnitine and water complex (1:1:1),
    a zoledronic acid, o-lauroyl-L-carnitine, and water complex (1:1:1),
    a zoledronic acid, o-decanoyl-L-carnitine, and water complex (1:1:1),
    a zoledronic acid, o-octanoyl-L-carnitine, and water complex (1:1:1),
    a zoledronic acid, o-octanoyl-L-carnitine, and water complex (1:1:1.5), and
    a zoledronic, L-carnitine, and water complex (1:1:1) comprising the steps of:
    slurrying zoledronic acid and L-carnitine or a fatty acid derivative of L-carnitine in water, an organic solvent or a water-organic solvent mixture; or
    grinding zoledronic acid and L-carnitine or a fatty acid derivative of L-carnitine in the presence of water, an organic solvent or a water-organic solvent mixture; and
    evaporating the water, an organic solvent or a water-organic solvent mixture to form the crystalline form of zoledronic acid.

10. A crystalline form of zoledronic acid according to claim 1 selected from a zoledronic acid L-carnitine hydrated complex.

11. A crystalline form of zoledronic acid according to claim 1 selected from a zoledronic acid L-carnitine complex.

12. A crystalline form of zoledronic acid according to claim 1 selected from a zoledronic acid, o-palmitoyl-L-carnitine, and water complex (1:1:1).

13. A crystalline form of zoledronic acid according to claim 1 selected from a zoledronic acid, o-myristoyl-L-carnitine, and water complex (1:1:1).

14. A crystalline form of zoledronic acid according to claim 1 selected from a zoledronic acid, o-lauroyl-L-carnitine, and water complex (1:1:1).

15. A crystalline form of zoledronic acid according to claim 1 selected from a zoledronic acid, o-decanoyl-L-carnitine, and water complex (1:1:1).

16. A crystalline form of zoledronic acid according to claim 1 selected from a zoledronic acid, o-octanoyl-L-carnitine, and water complex (1:1:1).

17. A crystalline form of zoledronic acid according to claim 1 selected from a zoledronic acid, o-octanoyl-L-carnitine, and water complex (1:1:1.5).

18. A crystalline form of zoledronic acid according to claim 1 selected from a zoledronic, L-carnitine, and water complex (1:1:1).

* * * * *